US010561536B2

(12) United States Patent
Holm et al.

(10) Patent No.: US 10,561,536 B2
(45) Date of Patent: Feb. 18, 2020

(54) CONFORMABLE DRAPE COVER DRESSING

(71) Applicant: 3M INNOVATIVE PROPERTIES COMPANY, St. Paul, MN (US)

(72) Inventors: David R. Holm, Hudson, WI (US); Richard L. Jacobson, Stillwater, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 32 days.

(21) Appl. No.: 15/107,490

(22) PCT Filed: Dec. 22, 2014

(86) PCT No.: PCT/US2014/071788
§ 371 (c)(1),
(2) Date: Jun. 23, 2016

(87) PCT Pub. No.: WO2015/102981
PCT Pub. Date: Jul. 9, 2015

(65) Prior Publication Data
US 2016/0317358 A1    Nov. 3, 2016

Related U.S. Application Data

(60) Provisional application No. 61/992,360, filed on Dec. 31, 2013.

(51) Int. Cl.
*A61F 13/02* (2006.01)
(52) U.S. Cl.
CPC ........ *A61F 13/024* (2013.01); *A61F 13/0226* (2013.01); *A61F 13/0236* (2013.01); *A61F 13/0259* (2013.01)
(58) Field of Classification Search
CPC .............. A61F 13/0226; A61F 13/0259; A61F 15/005; A61F 13/0236; A61F 2013/00578;

(Continued)

(56) References Cited

U.S. PATENT DOCUMENTS

RE24,906 E    12/1960  Ulrich
3,389,827 A    6/1968  Abere et al.
(Continued)

FOREIGN PATENT DOCUMENTS

EP    2 258 325    12/2010
JP    2003-102774    4/2003
(Continued)

OTHER PUBLICATIONS

Fey, M. D. et al.; "Chapter 18—Silicone Release Coatings"; Handbook of Pressure Sensitive Adhesive Technology; Van Nostrand-Reinhold; 1982; pp. 384-403.

*Primary Examiner* — Anna K Kinsaul
*Assistant Examiner* — Caitlin A Carreiro
(74) *Attorney, Agent, or Firm* — 3M Innovative Properties Company; Trisha D. Adamson

(57) ABSTRACT

A conformable wound dressing system that includes a wound dressing and a dressing support layer. The wound dressing includes a backing having two major surfaces and a perimeter that includes first and second lateral edges, an adhesive disposed on one major surface of the backing and the dressing support layer removably mounted on the other major surface. The dressing support layer includes juxtaposed first and second sections that define a gap between them. Each section comprises a medial portion and at least four spokes extending therefrom toward a lateral edge. The at least four spokes include two outer spokes and at least two spaced-apart inner spokes. At least two of the at least four spokes of each section extend beyond the lateral edge to form peripheral support layer tabs.

20 Claims, 25 Drawing Sheets

(58) Field of Classification Search
CPC .. A61F 2013/00817; A61F 2013/00829; A61F 13/024; A61F 2013/00553; A61F 2013/00561; A61F 2013/00608; A61B 2046/205
USPC .......... 602/42, 43, 52, 54, 57, 58; D24/189; 424/445; 604/304, 307; 128/888
See application file for complete search history.

(56) References Cited

U.S. PATENT DOCUMENTS

| | | | |
|---|---|---|---|
| 3,645,835 | A | 2/1972 | Hodgson |
| 4,112,213 | A | 9/1978 | Waldman |
| 4,310,509 | A | 1/1982 | Berglund et al. |
| 4,323,557 | A | 4/1982 | Rosso et al. |
| 4,472,480 | A | 9/1984 | Olson |
| 4,737,410 | A | 4/1988 | Kantner |
| 5,088,483 | A | 2/1992 | Heinecke |
| 5,160,315 | A | 11/1992 | Heinecke et al. |
| 5,531,855 | A | 7/1996 | Heinecke et al. |
| 5,622,711 | A | 4/1997 | Chen |
| 5,633,010 | A | 5/1997 | Chen |
| 5,683,354 | A * | 11/1997 | Levy ............... A61F 13/105 128/880 |
| 6,171,985 | B1 | 1/2001 | Joseph et al. |
| 6,264,976 | B1 | 7/2001 | Heinecke et al. |
| 6,368,687 | B1 | 4/2002 | Joseph et al. |
| 6,461,467 | B2 | 10/2002 | Blatchford et al. |
| 6,838,589 | B2 | 1/2005 | Liedtke et al. |
| 7,518,031 | B2 | 4/2009 | Liedtke et al. |
| 8,084,665 | B2 | 12/2011 | Liedtke et al. |
| 8,110,718 | B2 | 2/2012 | Heinecke |
| 2004/0162512 | A1 * | 8/2004 | Liedtke ............ A61F 13/0203 602/59 |
| 2010/0006121 | A1 | 1/2010 | Baxter et al. |
| 2012/0283615 | A1 | 11/2012 | Malik et al. |

FOREIGN PATENT DOCUMENTS

| | | |
|---|---|---|
| JP | 2006-167129 | 6/2006 |
| JP | 2010-029242 | 2/2010 |
| WO | WO 1997/07760 | 3/1997 |
| WO | WO 1999/27975 | 6/1999 |
| WO | WO 2008/019310 | 2/2008 |
| WO | WO 2010/048078 | 4/2010 |
| WO | WO 2013/162680 | 10/2013 |

* cited by examiner

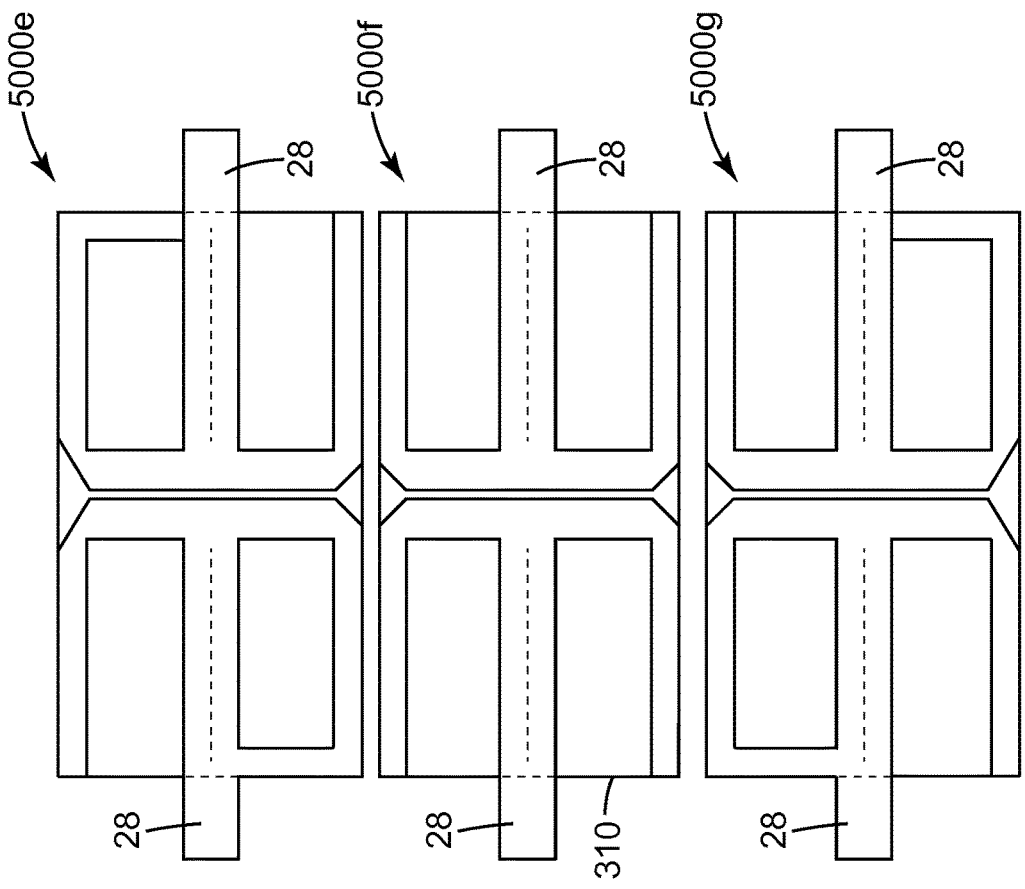
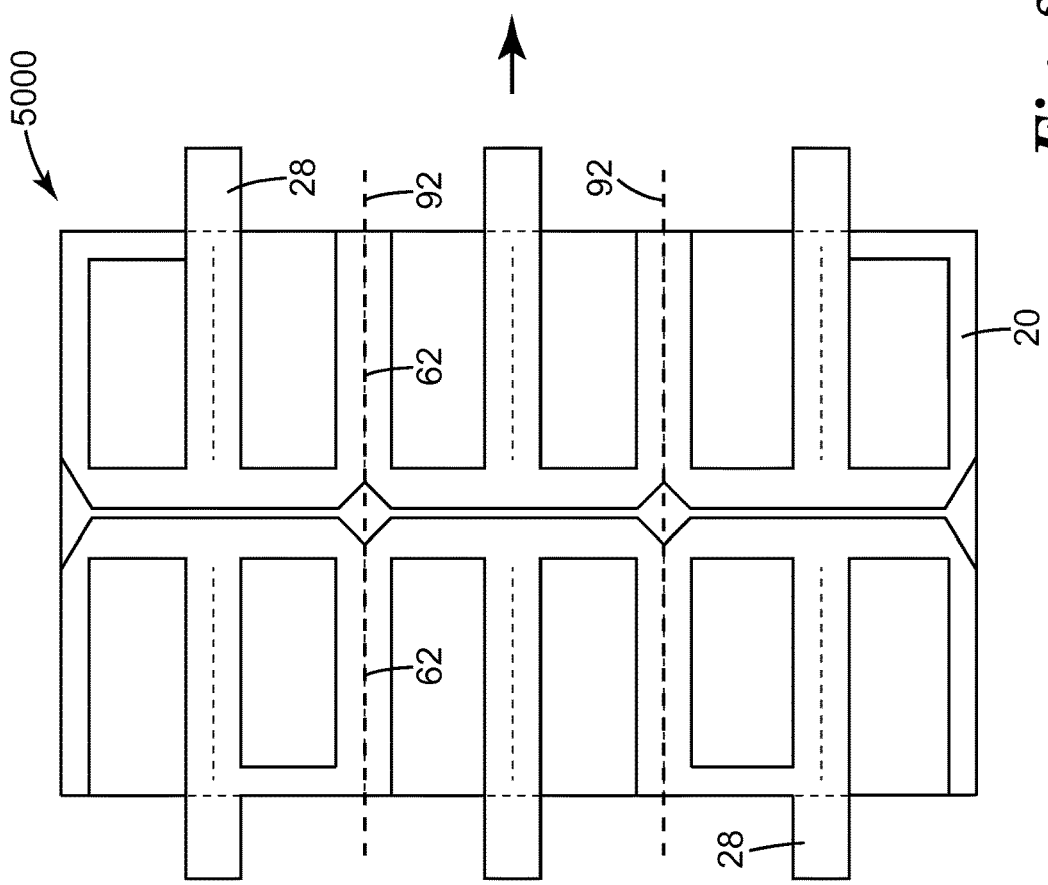
Fig. 21

CONFORMABLE DRAPE COVER DRESSING

CROSS REFERENCE TO RELATED APPLICATIONS

This application is a national stage filing under 35 U.S.C. 371 of PCT/US2014/071788, filed Dec. 22, 2014, which claims priority to U.S. Provisional Patent Application No. 61/922,360, filed Dec. 31, 2013, the disclosure of which is incorporated by reference in its entirety herein.

BACKGROUND

Transparent film dressings are widely used as protective layers over wounds because they facilitate healing in a moist environment while acting as a barrier to contaminating liquids and bacteria. The films are also used as surgical drapes because of their barrier properties. The film dressings are also used as drapes in negative pressure wound therapies to enable the application and maintenance of vacuum, which has been shown to improve wound healing. Dressings and drapes fitting the above description are available under a number of trade names such as TEGADERM (3M Company, St. Paul, Minn.), BIOCLUSIVE (Johnson & Johnson Company, New Brunswick, N.J.), OP-SITE (T. J. Smith & Nephew, Hull, England), and UNIPLEX (How Medica, Largo, Fla.).

In addition, various specifically-shaped transparent film dressings and corresponding delivery systems have been developed for applying the dressings to specific body parts or regions (e.g., a heel, the inner crease of an elbow, a shoulder, a sacral region).

The polymeric films used in those dressings and drapes generally are conformable, i.e., the films are extremely thin, flexible and supple. Typically, they are supplied with a releasable protective liner covering the adhesive coated surface of the film. When the liner is removed, the adhesive coated film tends to wrinkle and adhere to itself, interfering with the smooth, aseptic application of the dressing to a patient's skin. Various delivery systems have been proposed to address this problem.

SUMMARY

The present disclosure generally relates to conformable wound dressings that are applied to treatment sites in order to protect the wound site from microbial contamination or other disturbances while it heals or to enable the application and maintenance of vacuum to a wound. In particular, the present disclosure relates to a thin, elastic wound dressing and a carrier structure (e.g., a dressing support layer) removably bonded thereto, the carrier structure facilitating the application of the dressing to a treatment site. The inventive wound dressing system is not only adapted to be applied to relatively-large, highly-contoured treatment sites, it is also adapted to be cleaved along predefined lines in order to yield a plurality of cropped wound dressing systems that have all of the necessary features to apply them to relatively-smaller, contoured wound sites In one aspect, the present disclosure provides a wound dressing system. The wound dressing system can comprise a wound dressing having a first end a second end opposite the first end, and a longitudinal axis extending from the first end to the second end; and a dressing support layer. The wound dressing can comprise an elastic film backing and an adhesive disposed thereon. The backing can comprise a first major surface, a second major surface opposite the first major surface, and a perimeter that includes first and second lateral edges. The lateral edges extend from the first end to the second end. The adhesive is disposed on the first major surface. The dressing support layer can comprise juxtaposed first and second sections removably mounted on the second major surface of the backing, wherein the juxtaposed first and second sections define a gap between the sections. The gap can extend substantially from the first end to the second end. Each section comprises a medial portion extending from about the first end to about the second end, and at least four spokes extending therefrom toward a lateral edge. The at least four spokes comprise a first outer spoke extending substantially to the perimeter at the first end, a second outer spoke extending substantially to the perimeter at the second end, and at least two spaced-apart inner spokes disposed therebetween. At least two of the at least four spokes of each section extend beyond the lateral edge to form peripheral support layer tabs. The dressing support layer defines a plurality of covered portions and uncovered portions of the backing.

In any of the above embodiments, the first and second lateral edges can extend substantially parallel to the longitudinal axis. In any of the above embodiments, at least one of the inner spokes of the first section extends toward the first lateral edge substantially opposite one of the inner spokes of the second section. In any of these embodiments, at least one of the inner spokes of the first section and a corresponding inner spoke opposite thereof in the second section each comprises a visible indicium.

In another aspect, the present disclosure provides a method. The method can comprise cleaving the wound dressing system of any one of the preceding embodiments wherein at least one of the inner spokes of the first section extends toward the first lateral edge substantially opposite one of the inner spokes of the second section and wherein at least one of the inner spokes of the first section and a corresponding inner spoke opposite thereof in the second section each comprises a visible indicium. Cleaving the wound dressing system comprises cleaving the wound dressing along a line substantially defined by the gap to produce a plurality of cropped wound dressing systems, each cropped wound dressing system comprising a cropped wound dressing and at least one peripheral support layer tab. The method further can comprise applying the cropped wound dressing of one of the cropped wound dressing systems to a treatment site.

In another aspect, the present disclosure provides a method. The method can comprise cleaving the wound dressing system of any one of the preceding embodiments wherein at least one of the inner spokes of the first section extends toward the second lateral edge substantially opposite one of the inner spokes of the second section and wherein at least one of the inner spokes of the first section and a corresponding inner spoke opposite thereof in the second section each comprises a visible indicium. Cleaving the wound dressing comprises cleaving the dressing along any two or more visible indicia to produce a plurality of cropped wound dressing systems, each cropped wound dressing system comprising a cropped wound dressing and at least one peripheral support layer tab. The method further can comprise applying the cropped wound dressing of one of the cropped wound dressing systems to a treatment site.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, a tab can be interpreted to mean "one or more" tabs.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

BRIEF DESCRIPTION OF DRAWINGS

FIG. 21 is a plan view of the wound dressing system of FIG. 14 and four cropped wound dressing systems derived therefrom when the wound dressing system is cleaved along two predetermined paths.

DETAILED DESCRIPTION

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to conformable wound dressings. The wound dressings of the present disclosure are highly-conformable and have an adhesive disposed on one side. Thus, in the absence of a suitable carrier structure to support the dressings during placement at the treatment site, the dressings may be susceptible to folding back on themselves. The wound dressing system of the present disclosure provides structural features that not only support the dressing during application to a treatment site; they also enable the use of such conformable dressings to treat relatively-large, highly-contoured treatment sites. In addition, the structural features are adapted so that the wound dressing can be easily cleaved along predefined lines into a plurality of smaller wound dressing, each smaller wound dressing comprising all of the necessary structural features to facilitate its application to a smaller contoured treatment site.

Figure 1:
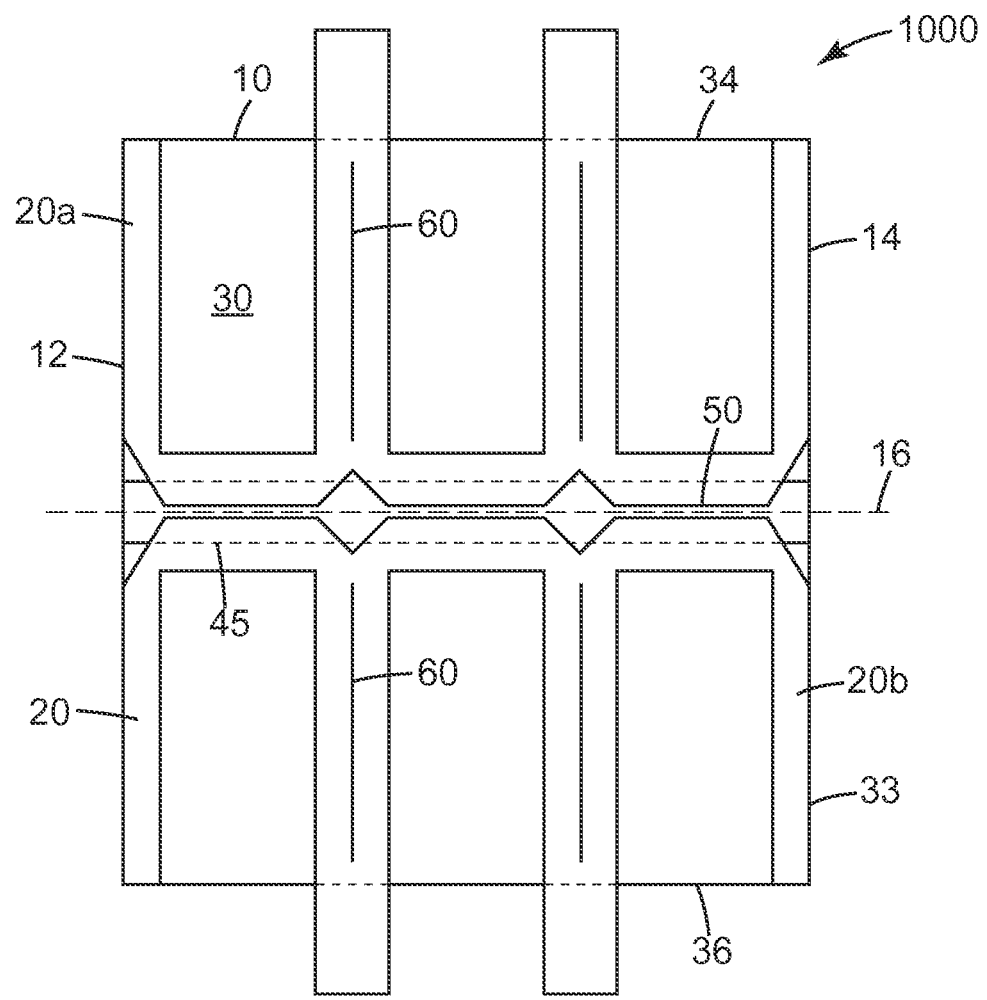
FIG. 1 is a plan view of one embodiment of a wound dressing system comprising a wound dressing and a dressing support layer according to the present disclosure.
Figure 2:
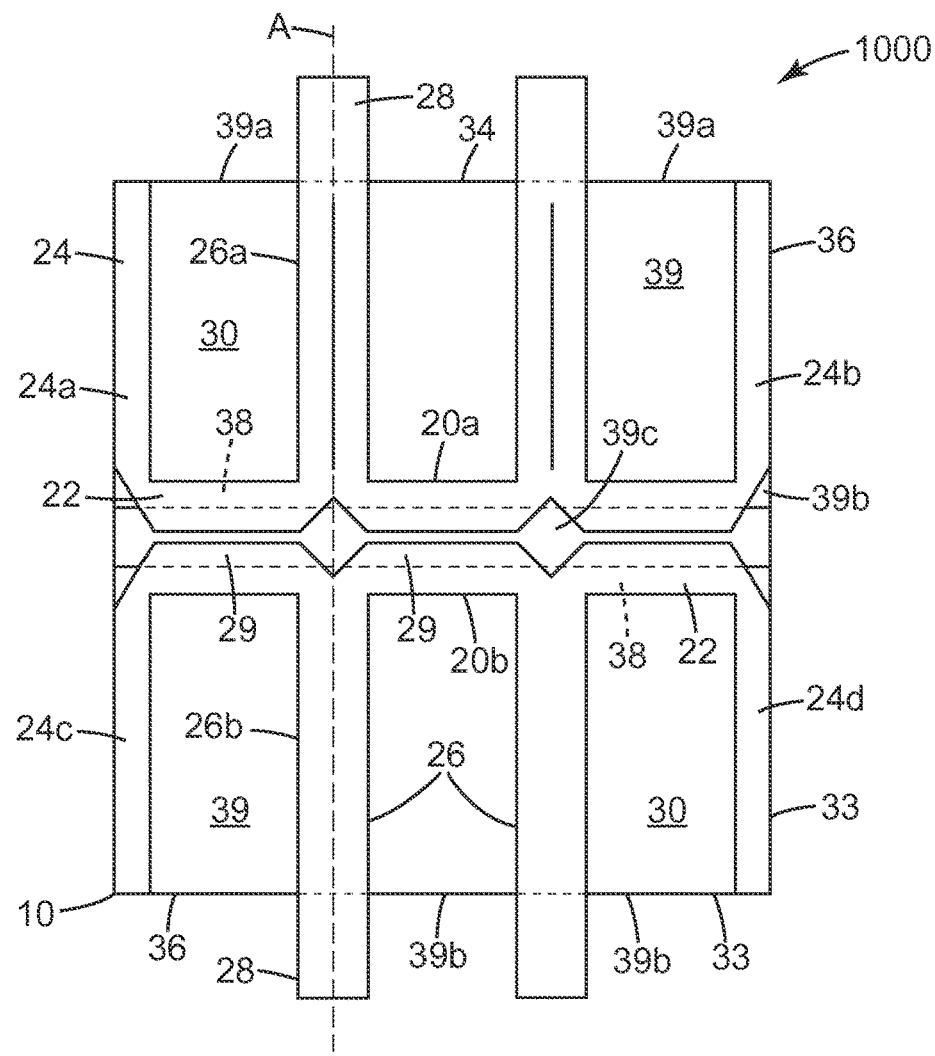
FIG. 2 is a plan view of the wound dressing system of FIG. 1 showing certain features of the backing and the dressing support layer.
Figure 3:
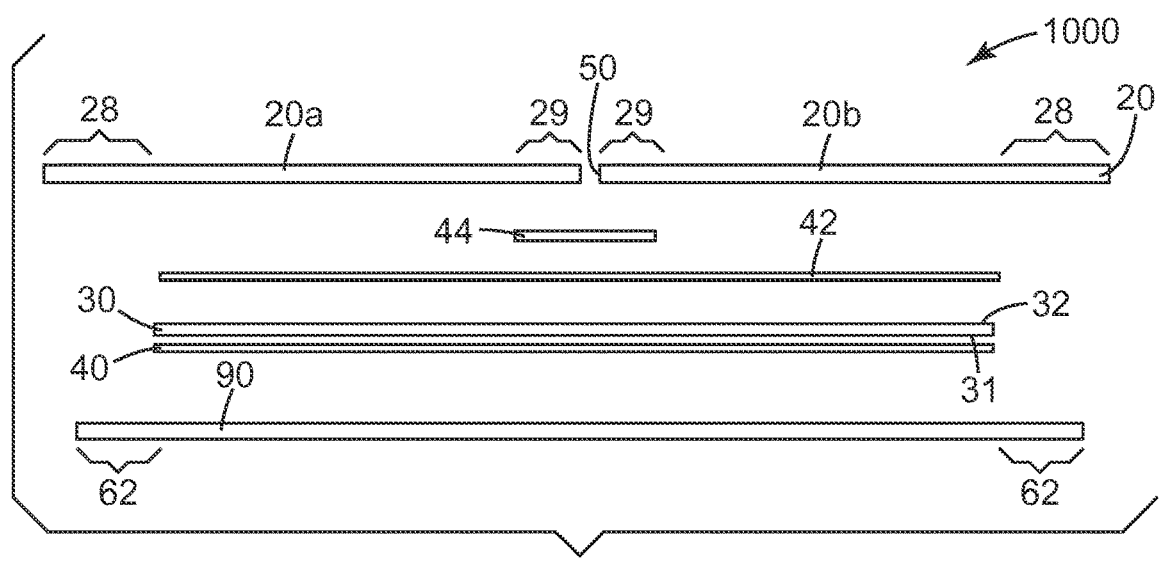
FIG. 3 is a side view of the wound dressing system of FIGS. 1 and 2.

FIGS. 1-3 depict one embodiment of a wound dressing system designated in its entirety by the reference numeral 1000. The system 1000 comprises a wound dressing 10 and a dressing support layer 20. The wound dressing 10 has a first end 12, a second end 14 opposite the first end, and a longitudinal axis 16 extending from the first end to the second end. In any embodiment, the longitudinal axis 16 can be coincident with the central axis of the wound dressing 10 (i.e., the longitudinal axis 16 is equidistant from the first and second lateral edges described below). The central axis is located approximately equidistant from the first and second lateral edges (discussed below) and extends from the first end to the second end of the wound dressing.

In any embodiment, the wound dressing 10 is the portion of the wound dressing system 1000 that is applied to a wound site (not shown) and is left on the wound site for a period of time. The dressing support layer 20 is the portion of the wound dressing system 1000 that facilitates the proper application of the wound dressing 10 to the wound site. Although removal of the dressing support layer 20 is not required, typically, the dressing support layer is removed after the wound dressing is applied to the wound.

The wound dressing 10 comprises an elastic film backing 30. The backing comprises a first major surface 31 and a second major surface 32 opposite the first major surface. The backing 30 has a perimeter 33 that includes a first lateral edge 34 and a second lateral edge 36. The first and second lateral edges (34 and 36, respectively) extend from the first end 12 to the second end 14 of the wound dressing 10. Preferably, the first and second lateral edges (24 and 26, respectively) extend substantially parallel to the longitudinal axis 16. The wound dressing 10 can be formed in a variety of shapes including, for example, a trapezoid, a rectangle, and a square, which can include rounded corners for each of the various shapes.

An adhesive 40 is disposed (e.g., as a coated layer) on the first major surface 31 of the backing 30. In any embodiment, preferably, the adhesive 40 is a pressure-sensitive adhesive (PSA). In any embodiment, a low adhesion coating (low adhesion backsize or LAB) 42 is provided (e.g., as a coated layer) on the second major surface 32 of the backing 30. A description of a preferred low adhesion coating for use with the backing of the present disclosure can be found in Example 1 of U.S. Pat. No. 5,531,855, which is incorporated herein by reference in its entirety. The low adhesion coating is compatible with a heat seal bond described herein. The low adhesion coating 42 reduces dressing changes due to unwanted dressing removal when tapes or devices are placed on the wound dressing 10 and then removed. In addition, the low adhesion coating reduces the surface friction of the wound dressing 10 on linen or other fabrics, thereby offering additional protection against the accidental removal of wound dressing 10 during use.

First major surface 31 is sometimes referred to as the "bottom face" or "patient-facing surface" of the backing 30, and second major surface 32 is sometimes referred to as the "top face" of the backing 30.

In any embodiment, the adhesive 40 may be applied as a continuous coating covering substantially the entire first major surface 31 of the backing 30. In any embodiment, the adhesive 40 may be coated discontinuously (e.g., in various types of porous patterns, not shown) on a portion of the first major surface 31.

Figure 4:
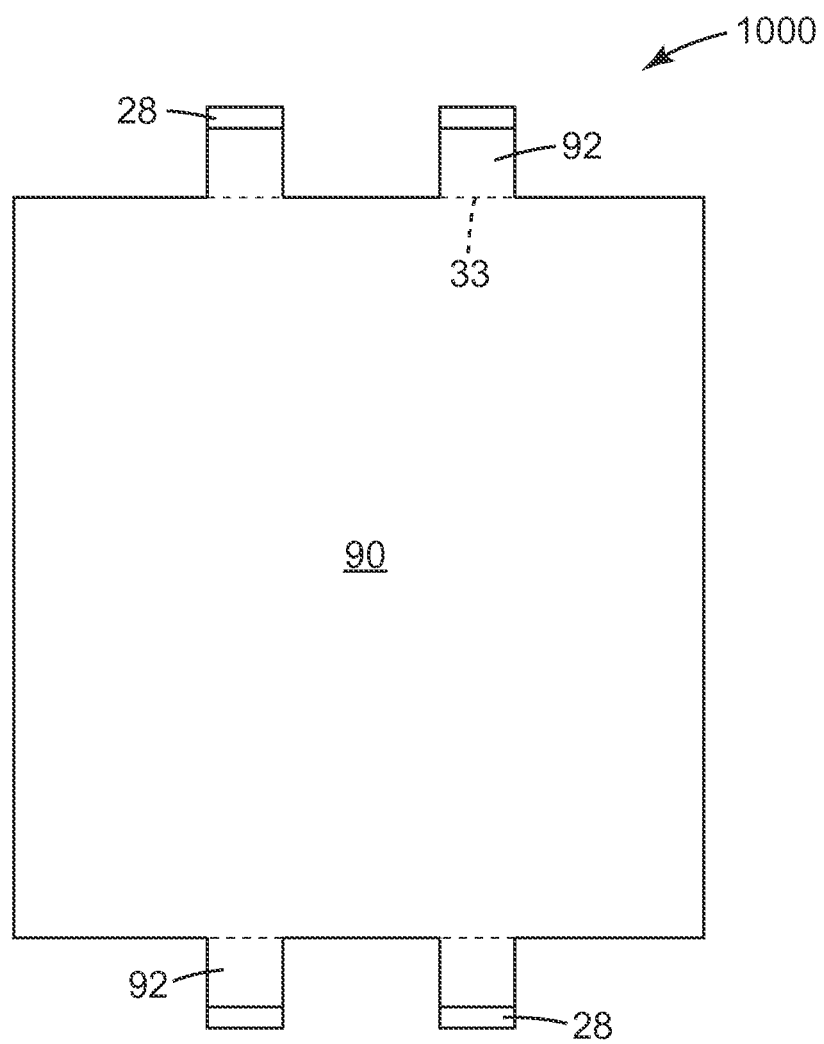
FIG. 4 is a bottom view of the wound dressing system of FIGS. 1 and 2.

In any embodiment, an optional release liner 90 is detachably attached to the exposed surface of adhesive 40 on the first major surface 31 of the backing 30. FIGS. 3 and 4 show one embodiment of a wound dressing system 1000 comprising one embodiment of a release liner according to the present disclosure. The release liner 90 covers the adhesive 40 until the operator is ready to apply the wound dressing 10 to a treatment surface. The release liner 90 may be a single piece or multiple piece release liner, and may be part of or laminated to a package (not shown) containing the wound dressing system, or merely enclosed along with the wound dressing 10 within the package. In any embodiment, the release liner 90 may comprise at least one release liner tab 92 that extends beyond the perimeter 33 of the backing. In any embodiment, the release liner tab 92 can overlap at least a portion of a peripheral support layer tab (peripheral support layer tab 28, discussed below). As used herein, a first piece can be said to "overlaps" or "overlie" a second piece if it covers a portion of either the second piece, or a portion of some third piece that is covered along its opposite side by the second piece. In other words, one piece can "overlap" or "overlie" another piece even though separated by a third piece.

The dressing support layer 20 of the wound dressing system comprises two juxtaposed sections, first section 20a and second section 20b, respectively. The first and second sections of the dressing support layer 20 are removably bonded onto the second major surface 32 of the backing 30, as described herein. The dressing support layer is preferably mounted (i.e., removably bonded) onto the second major surface 32 of the backing 30 (over low adhesion coating 42, if present) with a heat seal bond. The heat seal bond between the dressing support layer 20 and the backing 30 is stronger than the bond between the adhesive 40 and the release liner 90 so that the backing 30 remains attached to the dressing support layer 20 when release liner 90 is removed from the wound dressing 10. Once the release liner 90 and wound dressing 10 are separated, only the dressing support layer 20 and absorbent pad (described below), if present, support (i.e. provide rigidity to) the backing 30.

The juxtaposed first and second sections of the dressing support layer 20 define a gap 50 between the sections of the dressing support layer. The gap 50 extends substantially from the first end 12 to the second end 14 of the wound dressing 10. Thus, the gap 50 defines a visible line that can be used by an operator to guide a cutting process (e.g., with scissors) to cleave the wound dressing system 1000 from the first end to the second end to form two cropped wound dressing systems (not shown). Because the gap 50 substantially over laps the longitudinal axis 16 and, because the gap 50 also forms an axis of symmetry for the wound dressing system 1000, cleaving the wound dressing system 1000 along the line defined by the gap 50 yields two substantially identical cropped wound dressing systems (not shown).

In any embodiment, the gap 50 is a continuous gap. Wherein the gap 50 is continuous, the first and second sections of the dressing support layer 20 are physically separated by the gap 50. Alternatively, in any embodiment, the gap 50 is a discontinuous gap (e.g., a series of perforations, slits, or arrows) that extends from the first end 12 to the second end 14. In any embodiment, the gap 50 may simply comprise a slit (i.e., the gap may be less than about 1 mm, less than about 0.5 mm, or less than about 0.1 mm wide), as shown in the illustrated embodiment of FIG. 9.

Wherein the gap 50 is discontinuous, the first and second sections of the dressing support layer 20 are physically joined at the gap 50, although they are generally more easily separated (e.g., by tearing) than other portions of the dressing support layer (e.g., other portions that do not comprise the gap or another area of weakness in the dressing support layer 20 as described hereinbelow. In any embodiment, the gap 50 may be one or more controlled depth die cut, so as not to cut the backing 30, through the dressing support layer 20. Thus, the gap 50 provides a beginning point at which a portion of the dressing support layer 20 may be lifted from backing 30 and peeled away.

In any embodiment, at least a portion of the first section 20a of the dressing support layer 20 layer may overlap at least a portion of the second section 20b of the dressing support layer (not shown). In the embodiments wherein a portion of the first section overlaps a portion of the second section, the gap is defined by the edge of the second section.

Figure 14:
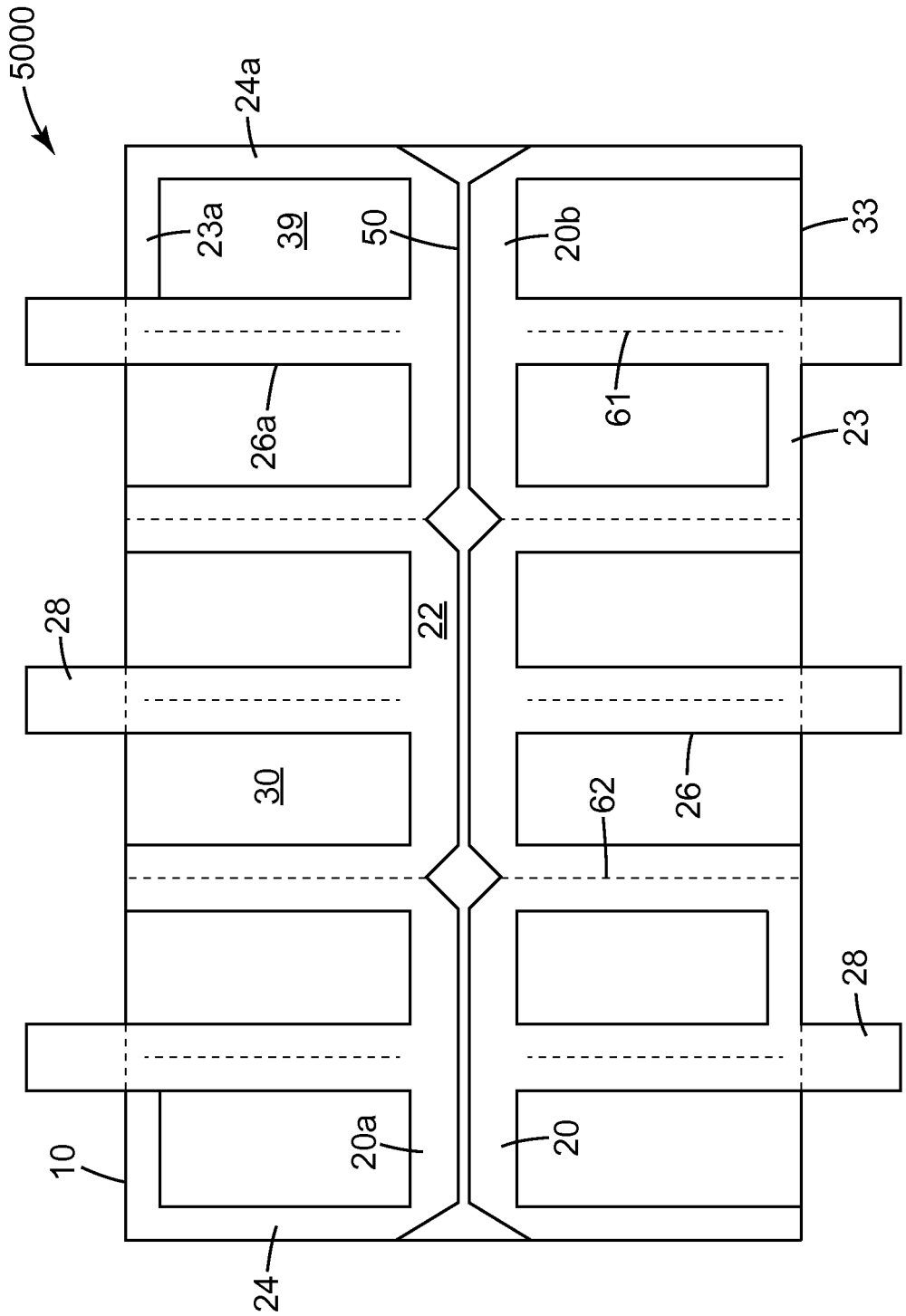
FIG. 14 is a plan view of another alternative embodiment of a wound dressing system according to the present disclosure, wherein the wound dressing system comprises a wound dressing and a dressing support layer according to the present disclosure.

Although not required, in any embodiment, the gap 50 may extend substantially along the central axis (which is coincident with the longitudinal axis 16) of the wound dressing 10, as illustrated in FIG. 1. Alternatively, in any embodiment, the gap 50 may extend along a line that is offset from the central axis, as shown in FIG. 14. In certain preferred embodiments, the path defined by the gap 50 is substantially parallel to the longitudinal axis 16 of the wound dressing 10.

Optionally, the dressing support layer 20 may comprise a visible indicium 61. In any embodiment, the dressing support layer may comprise a plurality of visible indicia 60, as shown in FIG. 1. In any embodiment, the visible indicia 60 may be visible lines (e.g., printed lines). It may be desired that the visible indicia 60 function as guides (e.g., define a line) for cleaving the wound dressing 10 into a plurality of cropped wound dressings, each cropped wound dressing having predetermined structural features as discussed herein. In any embodiment, a visible indicium 60 may be defined by a continuous mark (e.g., printed line). Alternatively, in any embodiment, a visible indicium 60 may be defined by a discontinuous mark (e.g., a printed dotted line).

In any embodiment, at least one of the visible indicia 60 comprises an area of weakness (e.g., a crease, a fold, a thinned portion (e.g., thinned by embossing), a perforation, a plurality of perforations, a slit, a plurality of slits). It may be desired that the area of weakness causes the dressing support layer to be more susceptible to bending or folding along a line defined by the visible indicium 60. Thus, the area of weakness facilitates conforming the wound dressing 10 to a contoured surface (e.g., a shoulder, a hip, a knee) in addition to supporting the wound dressing (e.g., to prevent it from folding back on itself) while it is being applied to the contoured surface. Thus, the area of weakness defines a portion of the dressing support layer that facilitates folding the wound dressing along a predefined path.

In any embodiment, a wound dressing of the present disclosure may comprise a bond-block zone to prevent bonding between a portion of the dressing support layer and the backing. FIG. 1 shows one embodiment of a bond-block zone 45 according to the present disclosure. In the illustrated embodiment of FIGS. 1-3, a bond-block agent 44 is applied (e.g., via a lamination process) to the bond-block zone 45. A non-limiting example of a suitable bond-block agent 44 is 3M MICROPORE Tape (available from 3M Company, St. Paul, Minn.).

The bond-block zone 45 overlaps the gap 50 and at least a part of the medial portion 22 of each section (20a and 20b) of the dressing support layer 20. Thus, the part of the medial portion 22 that overlaps the bond-block zone forms a plurality of medial support layer tabs 29 that do not adhere to the backing 30. Advantageously, the medial support layer tabs 29 can be grasped and pulled in order to handle the wound dressing system prior to application and to separate the dressing support layer 20, or a portion thereof, from the backing 30 before or after the wound dressing 10 is applied to a treatment surface (not shown). Although not required (see FIG. 17), in any embodiment, the bond-block zone is disposed proximate the central axis (which is coincident with the longitudinal axis 16) of the wound dressing 10, as illustrated in FIG. 1.

In any embodiment of the wound dressing system of the present disclosure, the dressing support layer comprises a number of structural features. Turning to FIGS. 1 and 2, each section (e.g., first section 20a and second section 20b) of the dressing support layer 20 comprises a medial portion 22 extending from about the first end 12 to about the second end 14 of the wound dressing 10. In any embodiment, the medial portion 22 of the first section 20a and/or second section 20b extends substantially parallel to the longitudinal axis 16. In any embodiment, the medial portion 22 of the first section 20a and/or second section 20b extends adjacent the longitudinal axis 16.

Extending from the medial portion 22 of each respective section of the dressing support layer 20 is a plurality of at least four spokes. The at least four spokes include two outer spokes 24 (e.g., the first section 20a of the dressing support layer 20 includes a first outer spoke 24a proximate the first end 12 and a second outer spoke 24b proximate the second end 14 and the second section 20b includes a first outer spoke 24c proximate the first end 12 and a second outer spoke 24d proximate the second end 14). In addition, the at least four spokes of each section of the dressing support layer 20 include two inner spokes 26.

The respective outer spokes 24 extend substantially to the perimeter 33 at the first and second ends (ends 12 and 14, respectively) of the wound dressing 10. "Extending substantially to the perimeter", as used herein, means the outer spokes 24 extend to a point close enough to the perimeter 33 that they provide enough support to the perimeter portion of the backing 30 to keep it from folding back on and adhering to itself when the liner 90, if present, is removed from the adhesive 40. In any embodiment, the outer spokes 24 extend all the way to the perimeter 33 of the backing 30.

In any embodiment, at least one of the outer spokes 24 of the dressing support layer 20 extends along the perimeter 33 at the first end 12 and/or the second end 14 of the wound dressing 10. For example first outer spoke 24a of the first section 20a and first outer spoke 24c of the second section 20b of the dressing support layer 20 of the wound dressing system 1000 (FIGS. 1 and 2) extend substantially along the perimeter 33 of the backing 30. In contrast, first outer spoke 24a of the first section 20a and first outer spoke 24c of the second section 20b of the dressing support layer 20 of the wound dressing system 1004 (FIG. 11, discussed below) do not extend substantially along the perimeter 33 of the backing 30.

In any embodiment at least one of the outer spokes 24 of the dressing support layer extends along at least 20% of the perimeter of the first end 12 or second end 14. In any embodiment, at least one of the outer spokes 24 of the dressing support layer 20 extends along at least 25% of the perimeter of the first end 12 or second end 14. In any embodiment, at least one of the outer spokes 24 of the dressing support layer 20 extends along at least 30% of the perimeter of the first end 12 or second end 14. In any embodiment, at least one of the outer spokes 24 of the dressing support layer 20 extends along at least 35% of the perimeter of the first end 12 or second end 14. In any embodiment, at least one of the outer spokes 24 of the dressing support layer 20 extends along at least 40% of the perimeter of the first end 12 or second end 14.

In any embodiment, each of the four outer spokes 24 of each section (e.g., first section 20a and second section 20b) of the dressing support layer 20 extends along at least 25% of the perimeter of the first end 12 or second end 14. In any embodiment, each of the four outer spokes 24 of each section (e.g., first section 20a and second section 20b) of the dressing support layer extends along at least 30% of the perimeter of the first end 12 or second end 14. In any embodiment, each of the four outer spokes 24 of each section (e.g., first section 20a and second section 20b) of the dressing support layer extends along at least 35% of the perimeter of the first end 12 or second end 14. In any embodiment, each of the four outer spokes 24 of the each section (e.g., first section 20a and second section 20b) of dressing support layer extends along at least 40% of the perimeter of the first end 12 or second end 14.

In any embodiment, at least one of the outer spokes 24 of the dressing support layer 20 extends along a portion of the first lateral edge 34 or second lateral edge 36. For example, the first outer spoke 24a of the first section 20a of the dressing support layer extends substantially along the perimeter 33 of the backing 30 at the first end 12 of the wound dressing 10. In addition, the first outer spoke 24a also extends along a portion of the first lateral edge 34. In any embodiment, both outer spokes 24 of the first section 20a and/or the second section 20b of the dressing support layer 20 extend along a portion of the first lateral edge 34 or the second lateral edge 36.

The at least four spokes extending from the medial portion 22 of each section (e.g., first section 20a and second section 20b) of the dressing support layer 20 include at least two spaced-apart inner spokes 26 disposed between the two outer spokes 24 of the section. "Spaced-apart inner spokes", as used herein refers to inner spokes that do not radiate from a common point at the medial portion of the dressing support layer (i.e., straight lines drawn through the longitudinal axis of the inner spokes 26, such as, for example, the straight lines defined by the visible indicia 60 of FIG. 1, do not intersect at the medial portion 22 of the dressing support layer 20). In any embodiment, the longitudinal axes of at least two of the two or more inner spokes 26 of either or both sections of the dressing support layer 20 extend substantially parallel to each other, as shown in the illustrated embodiment of FIGS. 1-2.

At least two of the at least four spokes of each section (e.g., first section 20a and second section 20b) of the dressing support layer 20 extend beyond a lateral edge (e.g., first lateral edge 34 or second lateral edge 36 to form peripheral support layer tabs 28. The peripheral support layer tabs 28 extend outwardly from the wound dressing 10 to provide structures that can be gripped by fingers to position the wound dressing while applying it to a patient and, additionally, to peel the wound dressing 10 from the release liner 90 before applying the dressing to the patient and/or to peel the dressing support layer from the wound dressing 10 after applying the dressing to the patient.

In any embodiment of a wound dressing system of the present disclosure, at least one spoke (e.g., an inner spoke or an outer spoke) extends along a line that is substantially perpendicular to the longitudinal axis of the wound dressing. In any embodiment, a plurality of spokes (e.g., a plurality of inner spokes, a plurality of outer spokes, or a combination thereof) extends along lines that are substantially perpendicular to the longitudinal axis of the wound dressing. In any embodiment, all of the spokes (e.g., inner spokes and outer spokes) extend along lines that are substantially perpendicular to the longitudinal axis of the wound dressing.

In any embodiment, the dressing support layer 20 defines a plurality of covered portions 38 and uncovered portions 39 of the backing 30. In any embodiment, the uncovered portions 39 include at least two uncovered portions 39a along the first lateral edge 34 of the backing 30 and at least two uncovered portions 39b along the second lateral edge 36 of the backing. Advantageously, the at least two uncovered portions of each lateral edge provides greater conformability of the wound dressing system prior to the removal of the dressing support layer, thereby facilitating the application of the wound dressing to a contoured surface and, in particular, to a large contoured surface. In addition, having uncovered portions of the lateral edges of the wound dressing system provides better visibility of the treatment site when applying the dressing and also facilitates conforming the edge of the wound dressing to a medical device such as a catheter, for example, that may be present on the surface of the treatment site. In addition, having uncovered portions of the lateral edges reduces the possibility that the dressing will be lifted off the skin during removal of the support layer.

The uncovered portions 39 (i.e., "windows") may be cut (e.g., controlled depth die cut) from a dressing support layer blank (not shown) to form a dressing support layer 20 having an uncovered portion 39 (i.e., window) exposing a portion of the top surface of the backing 30. The out or window portion (not shown) of the blank may be either removed during manufacturing or by the consumer.

The uncovered portions 39 of the backing 30 provide increased visibility in order for the operator to view the treatment site as the wound dressing 10 is being positioned over the treatment site and, subsequently applied to the site. In addition, the uncovered regions 39 provide increased flexibility when conforming the backing 30 to the treatment site during application of the wound dressing 10 to the treatment site. Thus, in any embodiment, the wound dressing system optionally comprises an uncovered region 39b along the perimeter 33 at the first end 12 and/or second end 14. Optionally, the uncovered region 39a at the first and/or second end can be proximate the gap 50. In any embodiment, the uncovered region 39a at the first end and/or second end can form part of the gap 50. Optionally, the gap 50 can comprise additional uncovered regions 39c. Although shown as triangular-shaped (uncovered region 39b) and diamond-shaped (uncovered region 39c), the uncovered regions at the first end, at the second end, or along the gap, may define any of a variety of shapes (e.g., circles, semi-circles, arcs, polygons).

In any embodiment, it may be desired that at least one inner spoke of the first section of the dressing support layer extends toward the first lateral edge substantially opposite one of the inner spokes of the second section. Returning to FIGS. 1 and 2, inner spoke 26a of the first section 20a and inner spoke 26b of the second section extend in substantially opposite directions toward the first and second lateral edges 34 and 36, respectively. Thus, first inner spoke 26a extends toward the first lateral edge 34 substantially opposite inner spoke 26b of the second section 20b. Because both inner spokes 26a and 26b have similar shapes and dimensions and both comprise visible indicia 60 that extend approximately along the longitudinal axes of the inner spokes, the visible indicia 60 of inner spokes 26a and 26b are substantially aligned and define a straight line "A" that extends from the first lateral edge 34 to the second lateral edge 36. Thus, the line "A" defines a visible line that can be used by an operator to guide a cutting process (e.g., with scissors) to cleave the wound dressing system 1000 from the first lateral edge 34 to the second lateral edge 36 to form two cropped wound dressing systems (not shown). Advantageously, cleaving the wound dressing system 1000 along the line "A" defined by the visible indicia of opposing inner spokes yields two cropped wound dressing systems that each comprise at least two peripheral support tabs, as discussed in detail below.

In any embodiment, it may be desired that a plurality of inner spokes of the first section of the dressing support layer extends toward the first lateral edge substantially opposite one of the inner spokes of the second section. In any embodiment, it may be desired that all of the inner spokes of the first section of the dressing support layer extends toward the first lateral edge substantially opposite one of the inner spokes of the second section. In these embodiments, the visible indicia, when present on opposing inner spokes of the first and second sections of the dressing support layer, can define at least one or a plurality of visible lines that can be used by an operator to guide a cutting process (e.g., with scissors) to cleave the wound dressing system from the first lateral edge to the second lateral edge to form a plurality of cropped wound dressing systems as described herein. In any embodiment of a wound dressing according to the present disclosure, each of the inner spokes can comprise a visible indicium.

Figure 5:
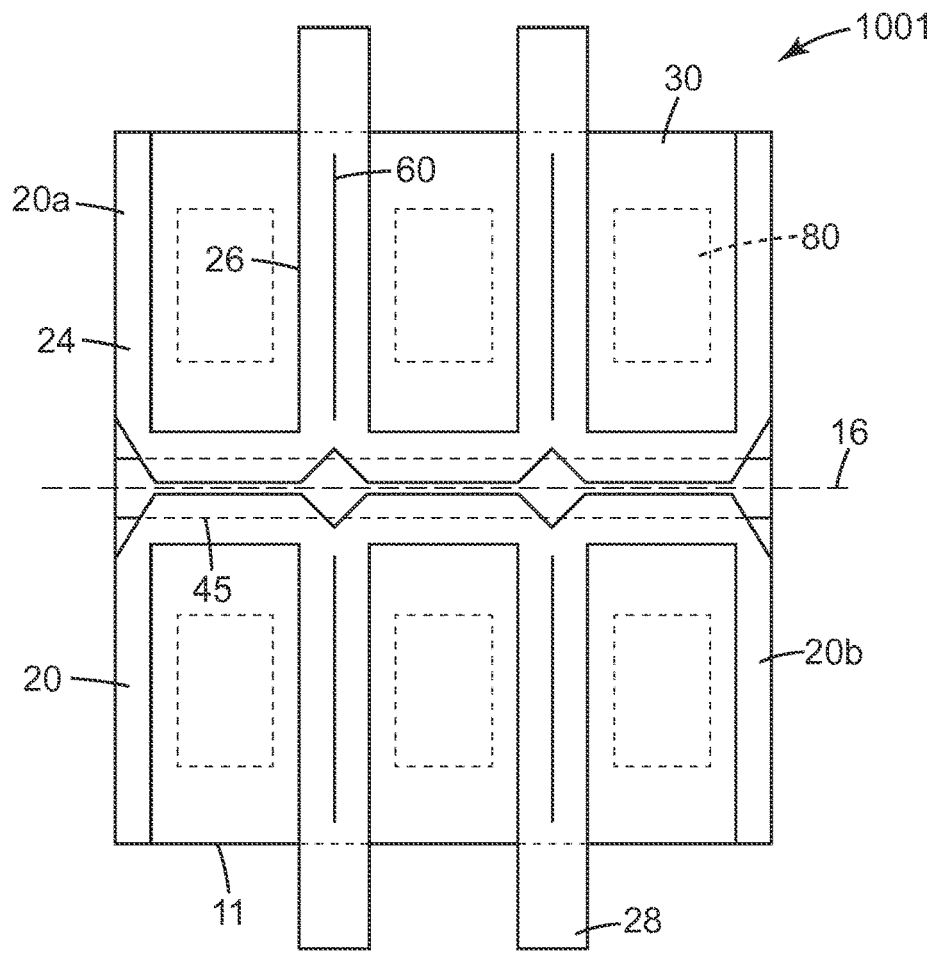
FIG. 5 is a plan view of an alternative embodiment of the wound dressing system of FIGS. 1-4, wherein the wound dressing further comprises a plurality of absorbent structures, wherein the dressing support layer does not overlay any of the absorbent structures.
Figure 6:
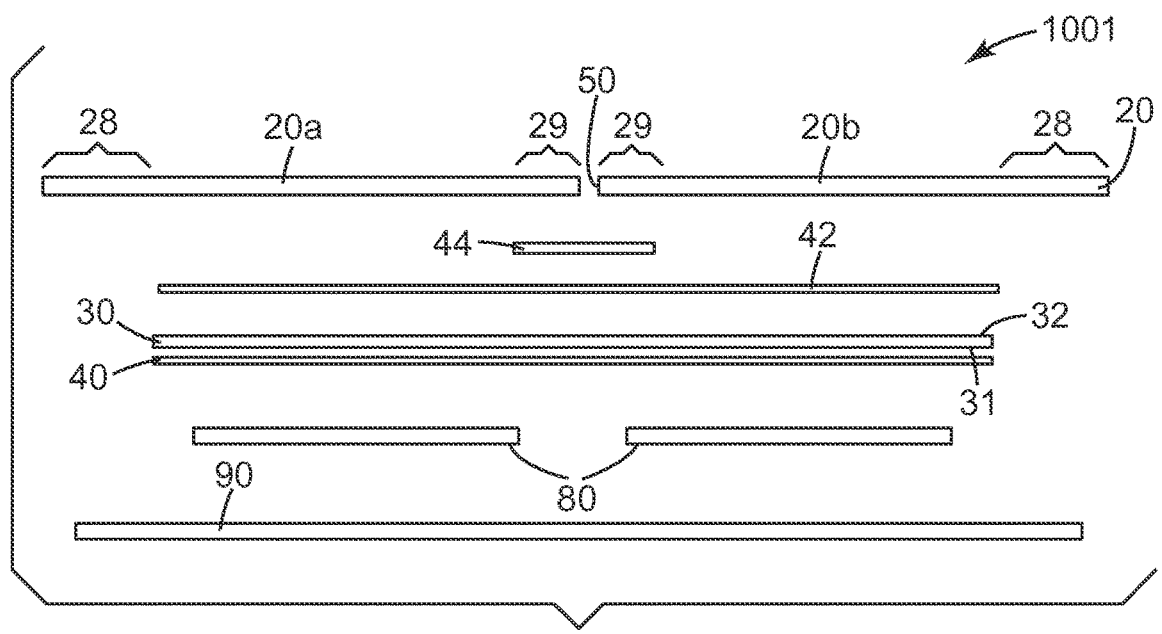
FIG. 6 is a side view of the wound dressing system of FIG. 5.

Optionally, in any embodiment, a wound dressing of the present disclosure comprises an absorbent pad. FIGS. 5-6 show one embodiment of a wound dressing system 1001 comprising an absorbent pad 80. The wound dressing system 1001 comprises a wound dressing 11 and a dressing support layer 20 as described herein. The wound dressing 11 comprises a longitudinal axis 16, a backing 30 having a first major surface 31, a second major surface 32 opposite the first major surface, and a bond-block zone 45. Disposed on the first major surface 31 is an adhesive 40. Adhered to the adhesive 40 and positioned between the adhesive 40 and the optional release liner 90 is a plurality of absorbent pads 80. Disposed on the second major surface 32 of the backing 30 are the optional low adhesion coating 42 and bond-block agent 44. Bonded to the second major surface 32 of the backing 30 is the dressing support layer 20 that comprises the first section 20a, second section 20b, optional visible indicia 60, peripheral support layer tabs 28, and medial support layer tabs 29. Located between the first section 20a and second section 20b is the gap 50, as described herein.

In any embodiment, the optional absorbent pad 80 of the wound dressing 11 is sometimes referred to as an "island pad" because the backing 30 extends substantially beyond the absorbent pad 80, typically beyond the entire periphery of the pad 80. For example, the length and width of the backing could be about 30 cm×21 cm, and the length and width of the absorbent pad could be about 6 cm×4 cm. The pressure sensitive adhesive 40 on the peripheral portion of the backing 30 not covered by the absorbent pad 80 may be adhered to the skin of a patient. This portion of the backing 30 is thus not supported or reinforced by the relatively heavy and stiff absorbent pad 80, and, absent the benefits of the invention, would be difficult to handle without folding, wrinkling or otherwise adhering to itself rather than adhering to the skin.

Although shown as generally rectangular-shaped in FIG. 5, the absorbent pad 80 may be provided in any one or more of a variety of shapes including, for example, a circle, an oval, a polygon, or an irregular shape. Although the rectangular absorbent pads 80 are shown in FIG. 5 as being oriented with their longitudinal dimension extending substantially perpendicular to the longitudinal axis of 16 of the wound dressing 11, one or more absorbent pad 80 alternatively can be oriented with its longitudinal dimension extending substantially parallel to the longitudinal axis 16 of the dressing 11, as shown in the wound dressing system 1002 of FIG. 7.

Figure 7:
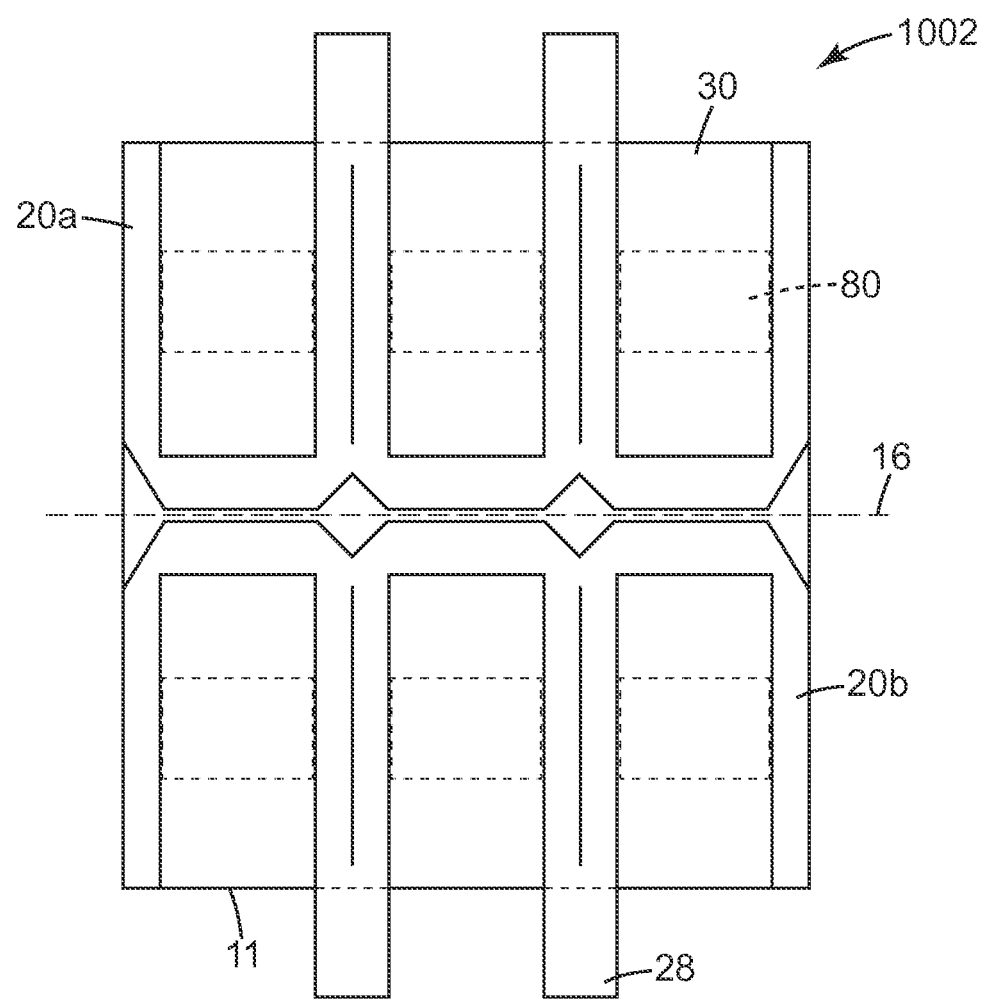
FIG. 7 is a plan view of an alternative embodiment of the wound dressing system of FIG. 5, wherein the absorbent structures are disposed in an alternative orientation with respect to the longitudinal axis.

The absorbent pads 80 of FIGS. 5-7 are not overlapped by either the first section 20a or the second section 20b of the dressing support layer. In any embodiment, one or more absorbent pad 80 of the wound dressing 11 may be overlapped by at least a portion of at least one spoke (e.g., outer spoke 24 and/or inner spoke 26) of at least one section (e.g., first section 20a or second section 20b) of the dressing support layer, as illustrated in the wound dressing system 1003 of FIG. 8.

Wound dressing systems of the present disclosure comprise a dressing support layer having two sections, wherein each section comprises a medial portion extending from about the first end to about the second end, and at least four spokes extending therefrom toward a lateral edge, as described hereinabove. In addition, at least two of the at least four spokes of each section extend beyond the lateral edge to form peripheral support layer tabs. FIGS. 1-8 show embodiments of the wound dressing system (e.g., wound dressing systems 1000, 1001, 1002, and 1003) wherein at least two of the at least four spokes of each section that comprise the peripheral support layer tabs are inner spokes. In any embodiment of a wound dressing system of the present disclosure, at least one of the at least two spokes that extends beyond the lateral edge of one of the sections can be an outer spoke, as shown in FIG. 9.

Figure 8:
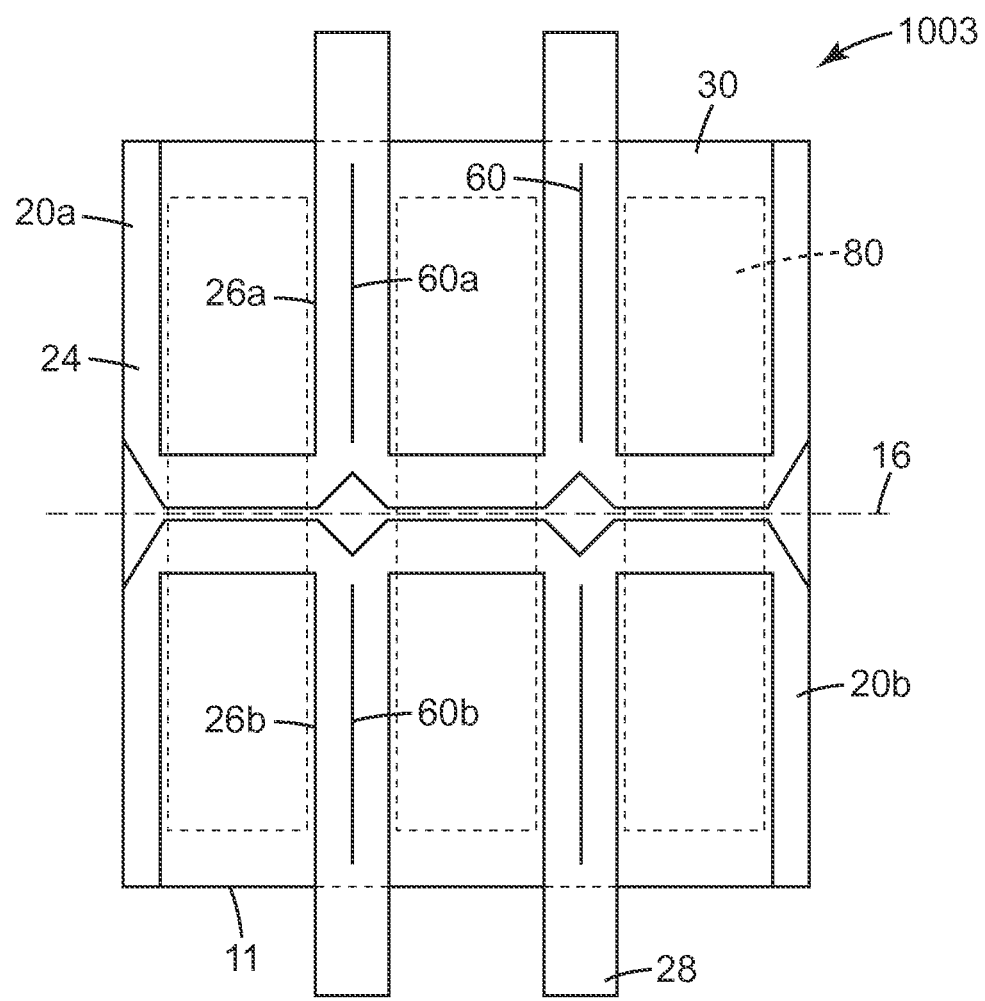
FIG. 8 is a plan view of an alternative embodiment of the wound dressing system of FIG. 5, wherein the dressing support layer overlaps portions of each absorbent structure

Also shown in FIG. 8 are two visible indicia (60a and 60b, respectively) that are formed in inner spokes (inner spokes 26a and 26b, respectively). The inner spokes (26a and 26b) are substantially aligned and extend in opposite directions away from the gap 50.

Figure 9:
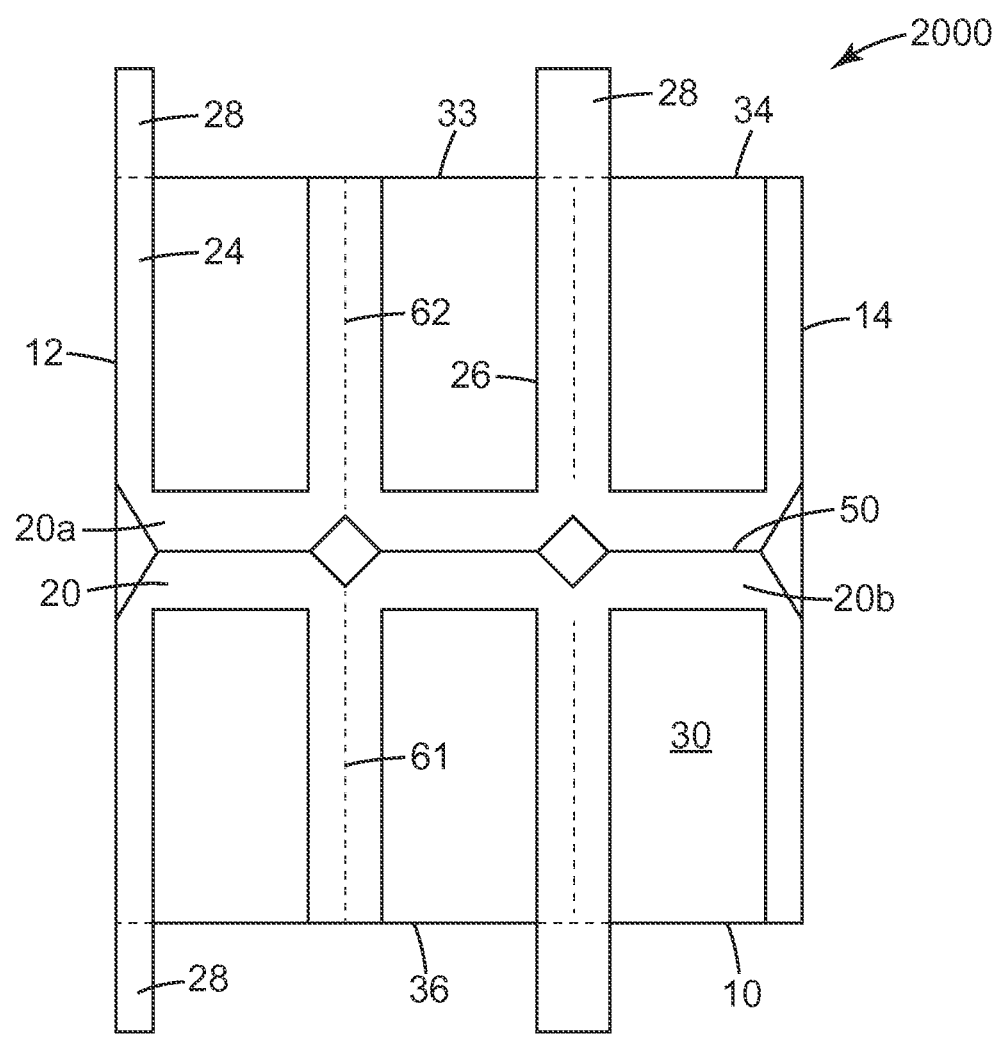
FIG. 9 is a plan view of another alternative embodiment of the wound dressing system of FIGS. 1-4, wherein the dressing support tabs are disposed in an alternative configuration.

FIG. 9 shows one embodiment of a wound dressing system 2000 comprising an outer spoke 24 of a section (e.g., first section 20a) of a dressing support layer 20 wherein the outer spoke 24 comprises a peripheral support layer tab 28. The outer spoke 24 is at the first end of the wound dressing 10. The outer spoke 24 further is one of the at least two spokes of the first section 20a that extends beyond the perimeter 33 of the backing 30 to form a peripheral support layer tab 28. Inner spoke 26 is the other spoke of the at least two spokes of the first section 20a that extends beyond the perimeter 33 of the backing 30 to form a peripheral support layer tab 28. Although it is not required that the first section 20a and second section 20b of a wound dressing of the present disclosure are symmetrical; the outer spoke of the second section 20b, opposite outer spoke 24 of the first section 20a, also extends beyond the perimeter 33 of the backing 30 to form a peripheral support layer tab 28.

Thus, in the illustrated embodiment of FIG. 9, the outer spoke 24 of the first section 20a, at the first end 12 of the wound dressing 10, comprises a peripheral support layer tab 28 and each of the other spokes of the first section, in order from the first end 12 to the second end 14, alternate between a spoke not having a peripheral support layer tab 28 and a spoke having a peripheral support layer tab 28. In addition, in the illustrated embodiment of FIG. 9, the outer spoke of the second section 20b, at the first end 12 of the wound dressing 10, comprises a peripheral support layer tab 28 and each of the other spokes of the second section, in order from the first end 12 to the second end 14, alternate between a spoke not having a peripheral support layer tab 28 and a spoke having a peripheral support layer tab 28.

Conversely, in any embodiment (not shown), the outer spoke of the first section, at the first end of the wound dressing, does not comprise a peripheral support layer tab and each of the other spokes of the first section, in order from the first end to the second end, alternate between a spoke having a peripheral support layer tab and a spoke not having a peripheral support layer tab. Additionally, or alternatively, the outer spoke of the second section, at the first end of the dressing, does not comprise a peripheral support layer tab and each of the other spokes of the second section, in order from the first end to the second end, alternate between a spoke having a peripheral support layer tab and a spoke not having a peripheral support layer tab. It could also be that all spokes have a tab extending beyond the perimeter. Also, we need to keep in mind that the perimeter of the backing along the lateral edges are not going to be straight as the film will extend up onto the tabs by a little (¼" or less)

Also shown in FIG. 9 is an embodiment of a visible indicium 61 formed by a discontinuous line (e.g., a printed dotted line, a printed dashed line, a series of perforations forming a line, a series of slits forming a line) and an embodiment of a visible indicium 62 that extends from the gap 50 between the sections of the dressing support layer to a peripheral edge (e.g., perimeter 33) of the backing 30. As discussed above, either visible indicium 61 or visible indicium 62 or both visible indicia 61 and 62 may comprise an area of weakness (e.g., a crease, a fold, a thinned portion (e.g., thinned by embossing), a perforation, a plurality of perforations, a slit, a plurality of slits).

Figure 10:
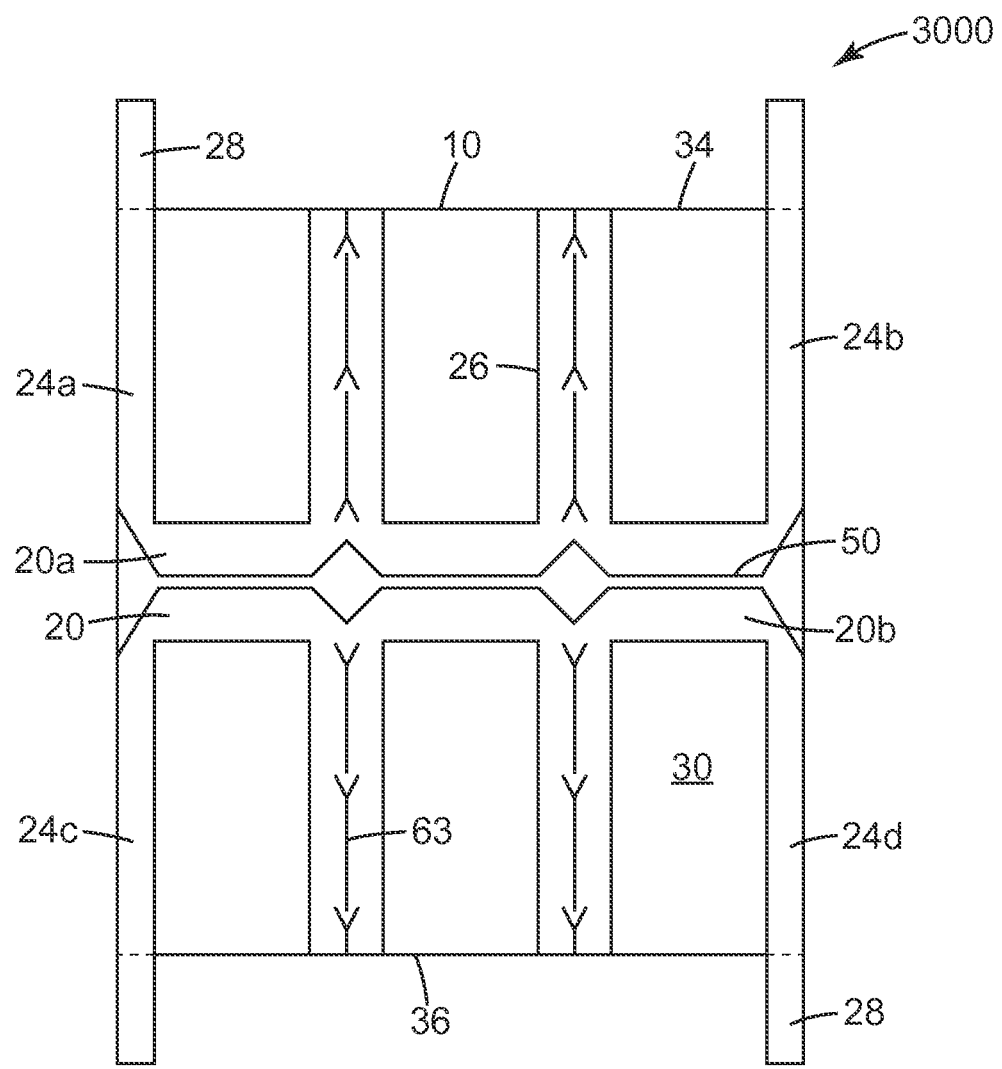
FIG. 10 is a plan view of yet another alternative embodiment of the wound dressing system of FIGS. 1-4, wherein the dressing support tabs are disposed in an another alternative configuration.

FIG. 10 shows one embodiment of a wound dressing system 3000 comprising a dressing support layer 20 wherein both outer spokes (e.g., outer spoke 24a and outer spoke 24b) of a section (e.g., first section 20a) of the dressing support layer 20 extends beyond the first lateral edge 34 of the backing 30 to form a peripheral support layer tab 28. The outer spokes 24a and 24b, thus, are two of the at least two spokes of the first section 20a that extends beyond the perimeter 33 of the backing 30 to form a peripheral support layer tab 28 of the wound dressing system 3000 of the present disclosure. Although it is not required that the first section 20a and second section 20b of a wound dressing of the present disclosure are symmetrical; the outer spokes (outer spokes 24c and 24d, respectively) of the second section 20b also extends beyond the perimeter 33 of the backing 30 to form peripheral support layer tabs 28. In the illustrated embodiment of FIG. 10, none of the inner spokes 26 of either the first section 20a or second section 20b of the dressings support layer 20 comprises a peripheral support layer tab 28.

Also shown in FIG. 10 is a visible indicium 63 that comprises a plurality of v-shaped cuts that facilitate cutting or tearing the dressing support layer 20 along a line defined by the visible indicium 63. As shown with the visible indicia 62 of in FIG. 9, the visible indicia 63 optionally extend from the gap 50 to the lateral edge (34 and 36, respectively).

Figure 11:
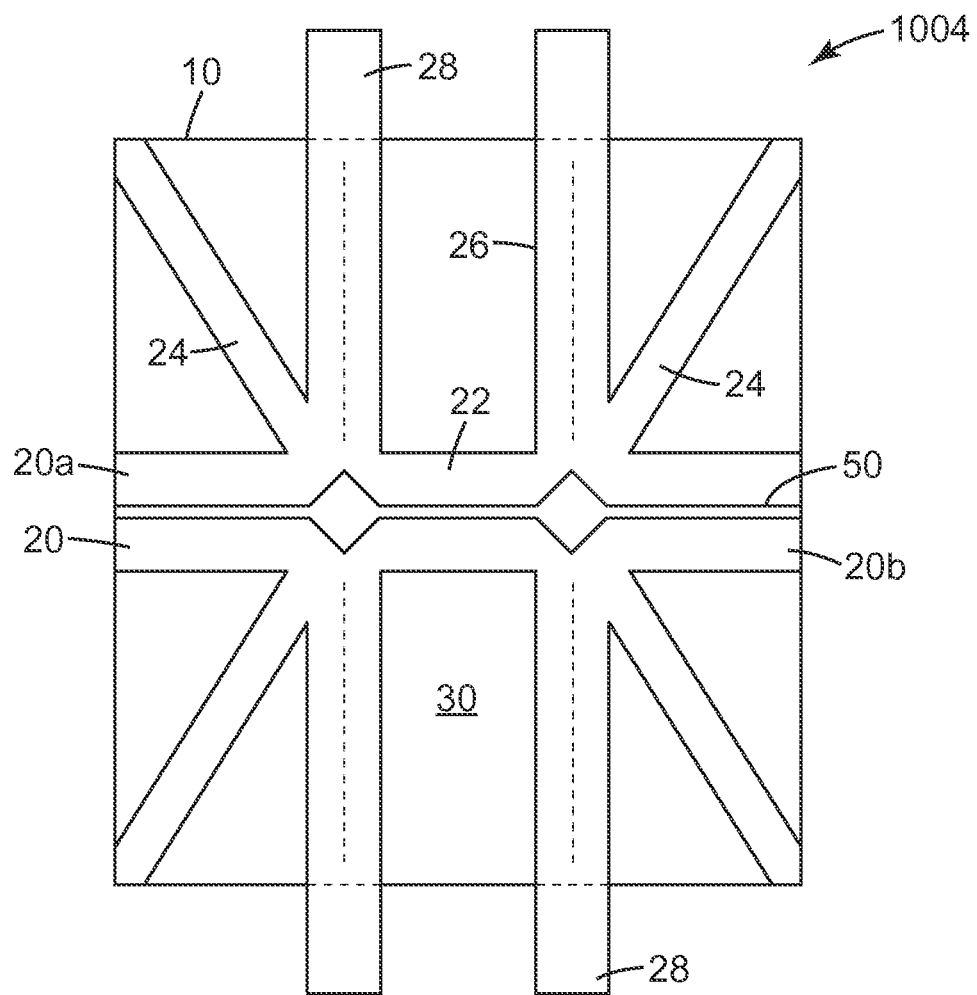
FIG. 11 is a plan view of yet another alternative embodiment of the wound dressing system of FIGS. 1-4, wherein the outer spokes of each section of the dressing support layer do not substantially extend along the first and second ends of the wound dressing.

In any embodiment of a wound dressing system of the present disclosure, at least one outer spoke can extend diagonally from the medial portion of the dressing support layer to a corner formed in the backing. FIG. 11 shows one embodiment of a wound dressing system 1004 comprising a plurality of outer spokes 24 that extend from the medial portion 22 of the dressing support layer 20 to one of the respective corners of the backing 30. In addition, each section (first section 20a and second section 20b, respectively) of the dressing support layer 20 comprises two inner spokes 26, each inner spoke comprising a peripheral support tab 28. The sections of the dressing support layer 20 are defined in part by a gap 50 disposed therebetween. It is contemplated that the outer spokes of this embodiment may further comprise dressing support layer tabs (not shown) that extend beyond the peripheral edge of the backing.

Figure 12:
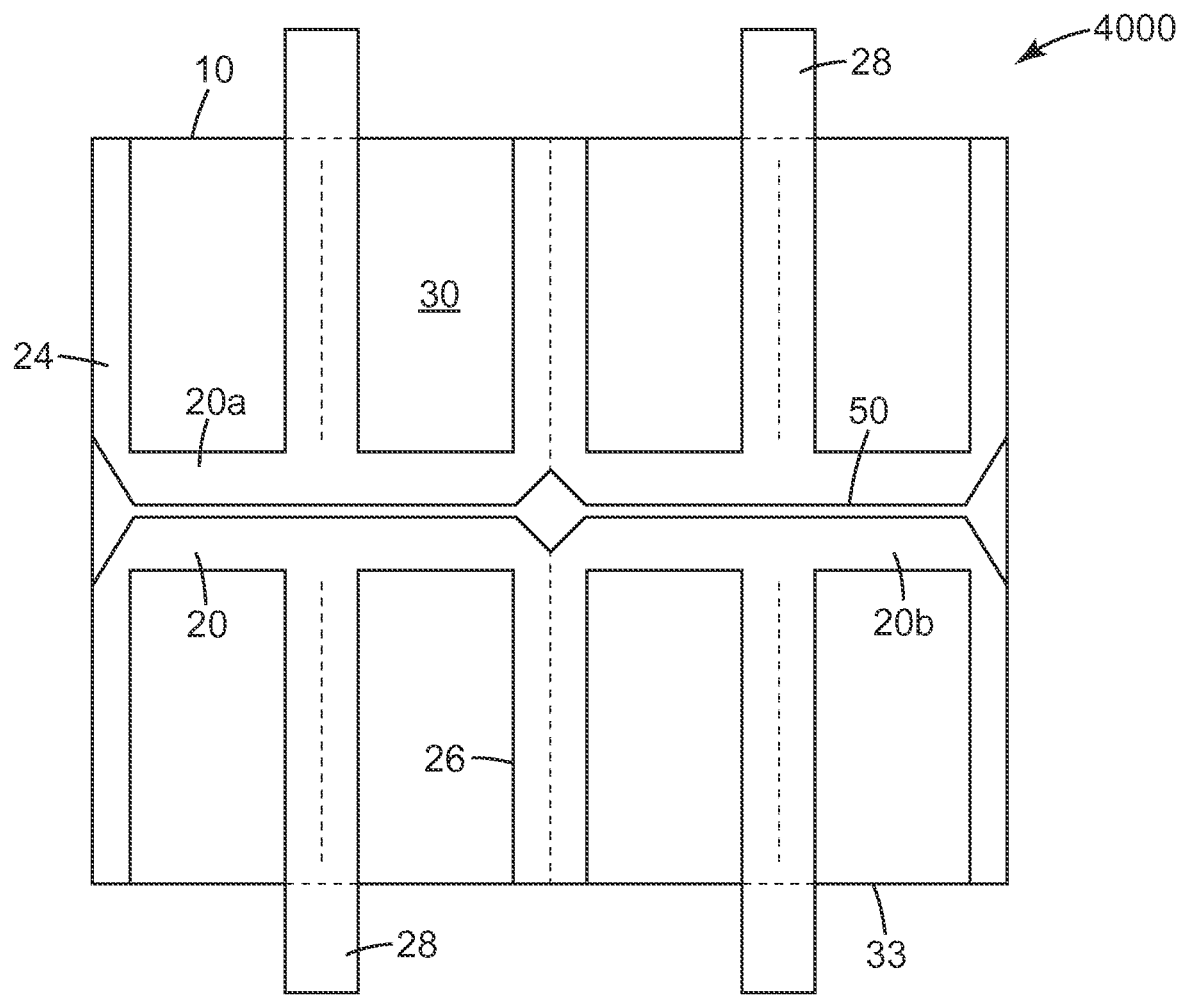
FIG. 12 is a plan view of an alternative embodiment of a wound dressing system according to the present disclosure, wherein the wound dressing system comprises a wound dressing and a dressing support layer according to the present disclosure.

In any embodiment, a wound dressing system of the present disclosure can comprise a dressing support layer having at least two sections, wherein each section comprises at least three spaced-apart inner spokes. FIG. 12 shows one embodiment of a wound dressing system 4000 comprising a wound dressing 10 and a dressing support layer 20 comprising two sections (first section 20a and second section 20b) bonded to the wound dressing 10. Each of the sections comprises two outer spokes 24 and three spaced-apart inner spokes 26. The sections of the dressing support layer 20 are defined in part by a gap 50 extending therebetween. At least two spokes (e.g., two inner spokes 26 of each section of the dressing support layer 20 comprise a peripheral support layer tab that extends beyond the peripheral edge of the backing 30. Advantageously, a wound dressing comprising a dressing support layer with at least three spaced-apart inner spokes provides the ability to support a highly flexible and conformable backing of a relatively large wound dressing, thereby making it possible to apply such a wound dressing to a relatively large treatment site of a relatively large portion of a body (e.g., a back, a leg, a chest, an abdomen, a knee, a hip). In addition, the wound dressing system can be cleaved from lateral edge to lateral edge along the visible indicia creating up to four separate dressing, each with a peripheral support layer tab on opposite ends for handling, each of the resulting cropped wound dressing systems having more than two portions of the perimeter where the support layer is not bonded to the backing.

Figure 13:
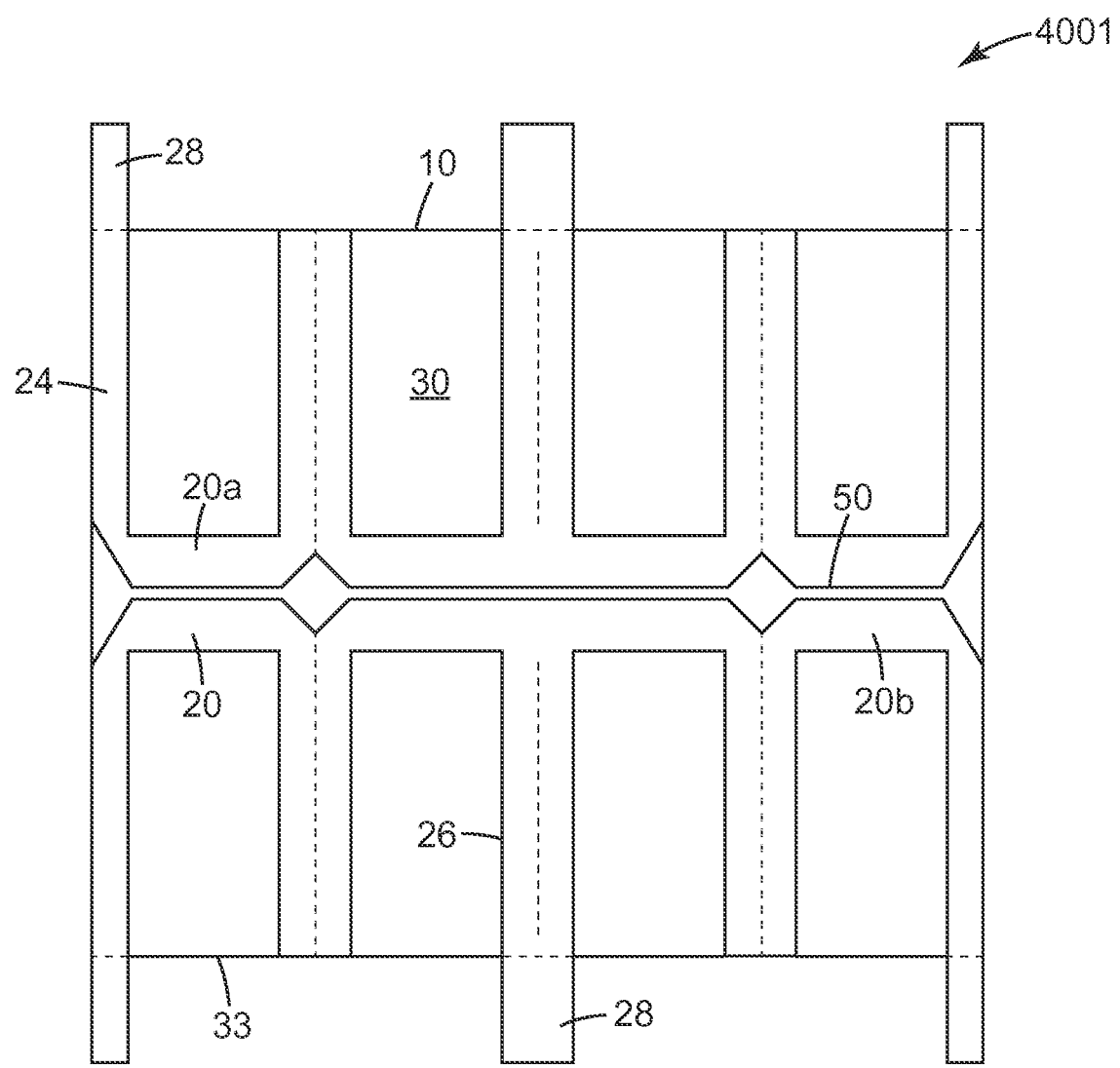
FIG. 13 is a plan view of an alternative embodiment of the wound dressing system of FIG. 12, wherein the dressing support tabs are disposed in an alternative configuration.

FIG. 13 show an alternative embodiment of a wound dressing system 4001 comprising a wound dressing 10 and a dressing support layer 20 comprising two sections (first section 20a and second section 20b) bonded to the wound dressing 10. Each of the sections comprises two outer spokes 24 and three spaced-apart inner spokes 26. The sections (20a and 20b, respectively) of the dressing support layer 20 are defined in part by a gap 50 extending therebetween. In contrast to the wound dressing system 4000 of FIG. 12, each section of the dressing support layer 20 of the wound dressing system 4001 comprises three spokes (e.g., both outer spokes 24 and one inner spoke) of each section having peripheral support layer tabs 28 that extends beyond the peripheral edge of the backing 30. The additional peripheral support layer tabs 28 provide the operator with the ability to use one or two of the plurality of tabs 28 during initial positioning of the wound dressing 10 over a relatively large wound site, while using other tabs 28 to position and complete the application of the dressing after an initial portion of the wound dressing 10 has been adhered to a portion of the relatively large wound site. Moreover, the additional tabs 28 provide the capability to cleave the wound dressing system 4001 into a plurality of cropped wound dressing systems (discussed below), each cropped wound dressing system having a dressing support layer with two sections, each section comprising at least two peripheral support layer tabs 28. Each of the cropped wound dressings system has at least three sides where the perimeter of the cropped dressings has a portion of the backing that is not bonded to the support layer. This aids in conformability and flexibility of the cropped wound dressing system.

In a preferred embodiment, a wound dressing system of the present disclosure comprises a wound dressing and a dressing support layer comprising two sections bonded to the wound dressing. Each of the sections comprises two outer spokes and at least five spaced-apart inner spokes. In addition, the dressing support layer comprises at least one bridge member that is spaced apart from the medial portion of the dressing support layer and forms a support structure extending between two adjacent spokes of a section of the dressing support layer.

FIG. 14 shows one embodiment of a wound dressing system 5000 that comprises a wound dressing 10 and a dressing support layer 20 comprising two sections (first section 20a and second section 20b) bonded to the wound dressing 10. Each of the sections comprises two outer spokes 24 and at least five spaced-apart inner spokes 26, as described herein. In addition, the dressing support layer 20 comprises a plurality of bridge members 23. The bridge members 23 are spaced apart from the medial portion 22 of the dressing support layer 20. Each of the bridge members 23 forms a support structure extending between two adjacent spokes of a section of the dressing support layer. For example bridge member 23a forms a support structure that supports the perimeter 33 of the dressing between the outer spoke 24a and the inner spoke 26a of the first section 20a of the dressing support layer 20. This feature is particularly beneficial when the wound dressing 10 is relatively large (e.g., measuring greater than or equal to about 20 cm along a lateral edge). Also shown in FIG. 14 are visible indicium 61 and visible indicium 62, as described hereinabove.

In the illustrated embodiment of FIG. 14, the bridge member 23a, the medial portion 22 of the dressing support layer 20, and the adjacent spokes 24a and 26a define an uncovered portion 39 of the backing.

The bridge member 23 in the illustrated embodiment of FIG. 14 are disposed proximate the perimeter 33 of the backing. It may be preferred that the bridge members 23 extend between a spoke with a peripheral support layer tab 28 and a spoke without a peripheral support layer tab. In any embodiment, the bridge member optionally may extend beyond the perimeter 33 of the backing 30 and may be contiguous with at least a portion of a peripheral support layer tab (not shown). Although the bridge members 23 are shown as extending completely between the adjacent spokes, it is contemplated that, in any embodiment, the bridge members 23 may be physically isolated from one or more of the adjacent spokes by a slit (not shown), for example. The one or more slit, if present, can impart additional flexibility to the dressing support layer, thereby facilitating the application of the wound dressing system to a highly-contoured surface (e.g., a knee or a shoulder).

Figure 15:
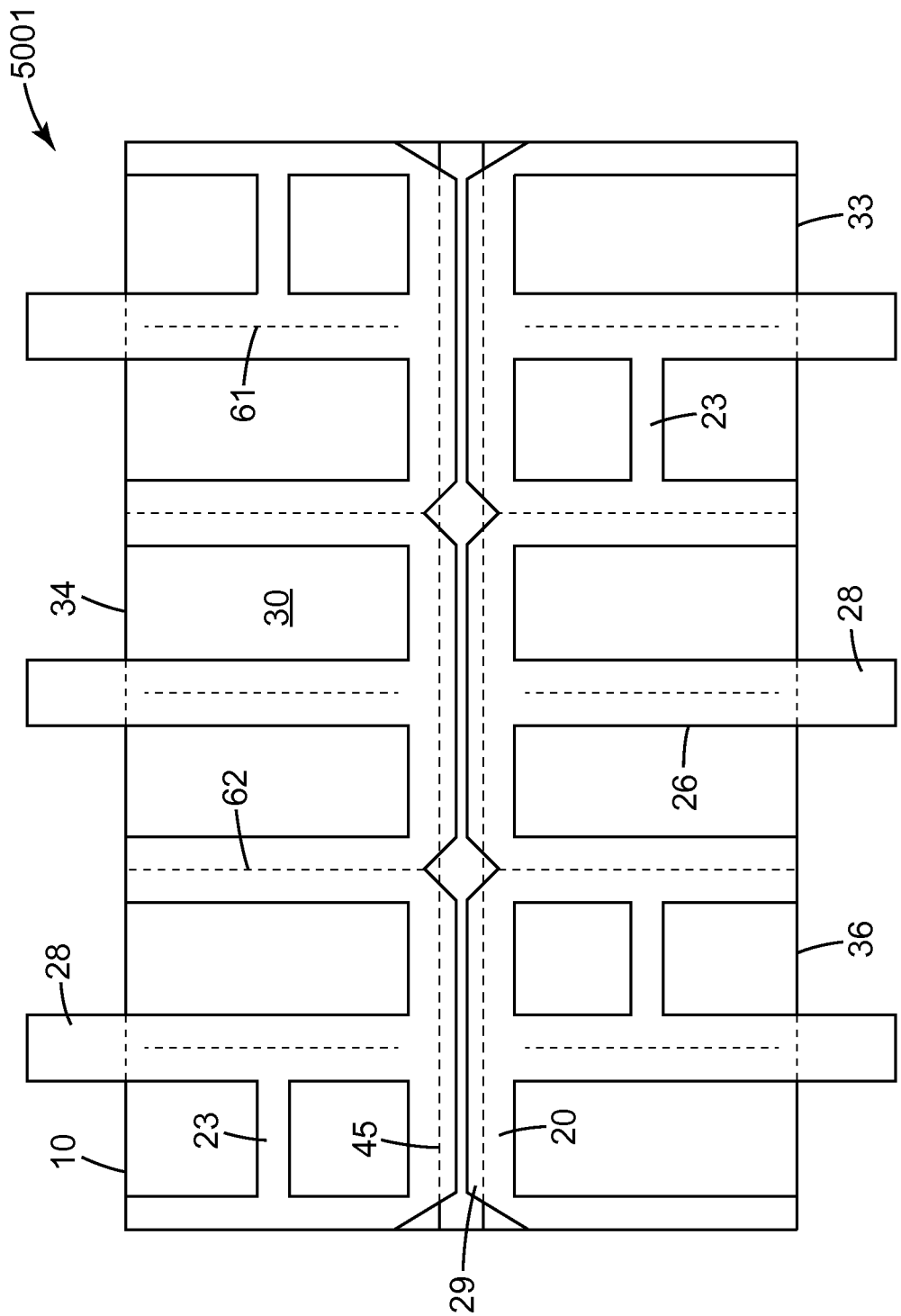
FIG. 15 is a plan view of an alternative embodiment of the wound dressing system of FIG. 14, wherein the dressing support bridge members are spaced apart from the lateral edges of the backing.

In any embodiment of a wound dressing system of the present disclosure, a bridge member can be disposed on the backing at a location that is spaced-apart from a lateral edge of the backing. FIG. 15 shows one embodiment of a wound dressing system 5001 comprising a dressing support layer 20 that includes a bridge member at a location that is spaced-apart from a lateral edge of the backing 30 (e.g., bridge member 23 of the first section 20a of the dressing support layer is spaced-apart from the first lateral edge 34 of the backing, as shown in FIG. 15). Advantageously, in these embodiments, the bridge member 23 still provides support to the backing 30 while it is being applied to a treatment surface, but it leaves the lateral edges (lateral edges 34 and 36, respectively) uncovered so that they can conform better to a medical device (e.g., a catheter) or a body part that is present at the treatment site. Also shown in FIG. 15 are bond block zone 45, peripheral support layer tabs 28, a medial support layer tab 29, visible indicium 61 and a visible indicium 62, all as described above.

Figure 16A:
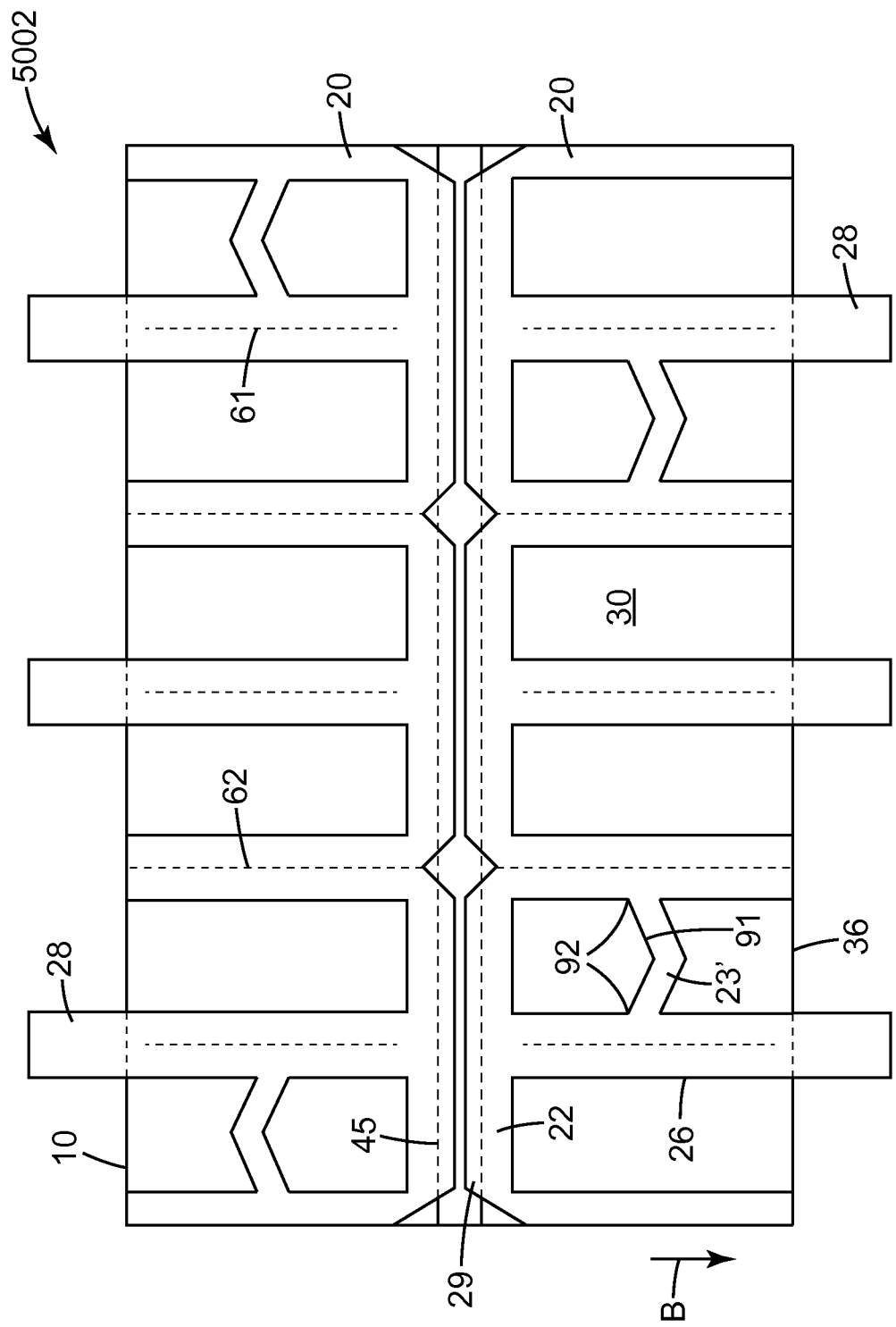
FIGS. 16a-c are plan views of alternative embodiments of the wound dressing system of FIG. 14, wherein the dressing support bridge members of each alternative embodiment comprise a proximate edge that extends away from the medial portion of the dressing support layer and toward the nearest lateral edge.

In any embodiment of a wound dressing system of the present disclosure comprising a dressing support layer section having a bridge member and a medial support layer tab, the bridge member can be configured in a manner that facilitates removal of the dressing support layer via applying a peeling force to the medial support layer tab. FIG. 16a shows an alternative embodiment (wound dressing system 5002) of the wound dressing system of FIG. 15. In the illustrated embodiment of FIG. 16a, the bridge members 23' are configured to facilitate removal of the dressing support layer 20. In the embodiment of FIG. 16a, the bridge members 23' are chevron-shaped.

The bridge members 23' of the dressing support layer 20 comprise a medial edge 91 proximate the medial portion 22 of the dressing support layer 20. The medial edge 91 comprises at least one closest point 92 that is closer to the medial portion 22 of the dressing support layer 20 than any other point on the medial edge of the bridge member 23'. The closest point 92 is located where the bridge member 23' abuts a spoke (e.g., inner spoke 26). Thus, when the medial support layer tab 29 is grasped and lifted away from the backing 30 and/or pulled in the direction of arrow "B", the closest point 92 is the first portion of the bridge member 23' that is separated from the backing, thereby facilitating the further separation of portions of the bridge member 23' that are located further away from the medial support layer tab. Advantageously, this configuration of the bridge member can prevent unintentional tearing of the dressing support layer and, potentially, separation of the bridge member from the spoke as the dressing support layer is removed from the backing. Also shown in FIG. 16a are bond block zone 45, peripheral support layer tab 28, a visible indicium 61 and a visible indicium 62, all as described above.

Figure 16B:
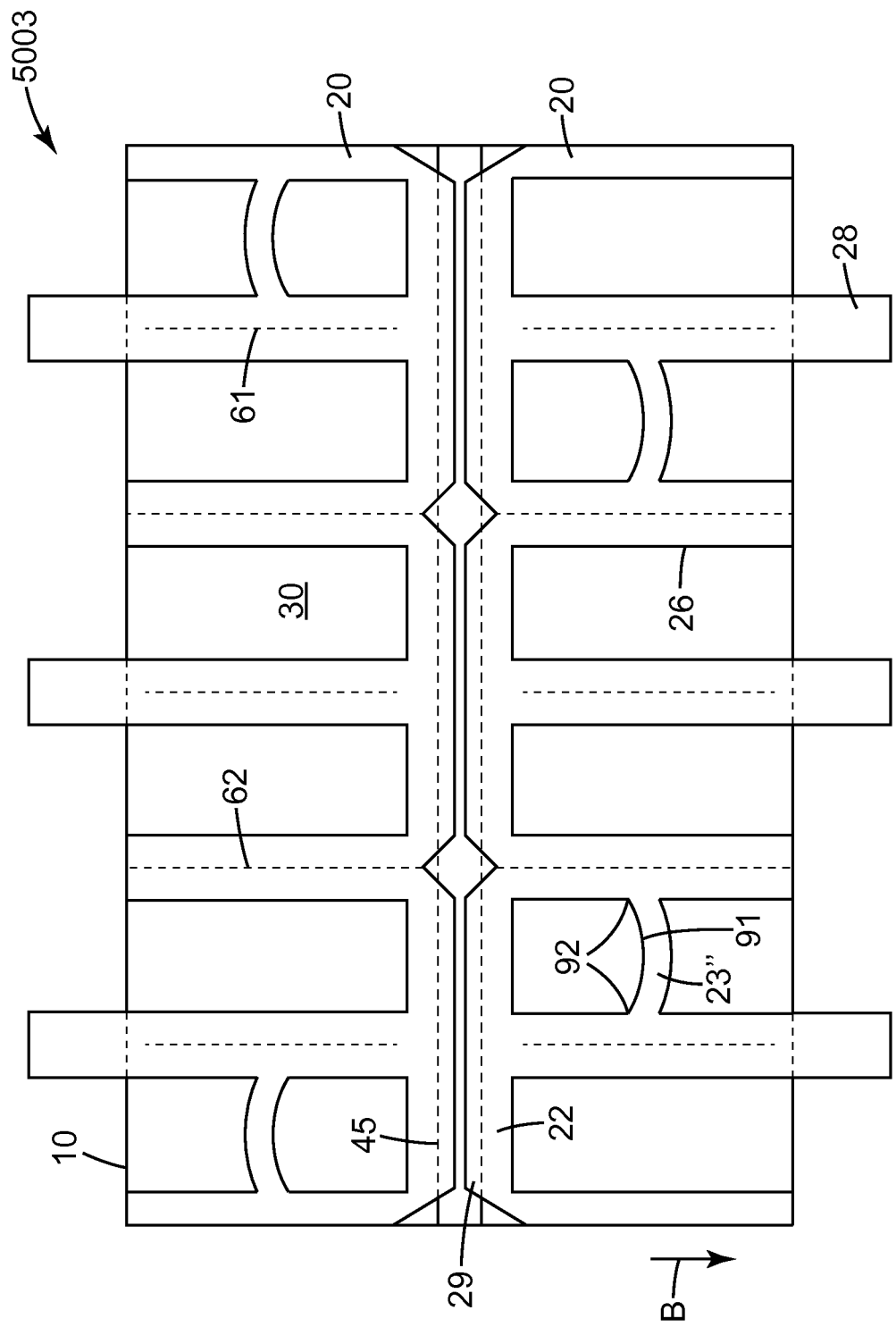

FIG. 16b shows an alternative embodiment (wound dressing system 5003) of the wound dressing system of FIG. 16a with bridge members configured to facilitate removal of the dressing support layer. In the embodiment of FIG. 16b, the bridge members 23' are arch-shaped. The bridge members 23" of the dressing support layer 20 comprise a medial edge 91 proximate the medial portion 22 of the dressing support layer 20. The medial edge 91 comprises at least one closest point 92 that is closer to the medial portion 22 of the dressing support layer 20 than any other point on the medial edge of the bridge member 23". The closest point 92 is located where the bridge member 23" abuts a spoke (e.g., inner spoke 26). Thus, when the medial support layer tab 29 is grasped and lifted away from the backing 30 and/or pulled in the direction of arrow "B", the closest point 92 is the first portion of the bridge member 23" that is separated from the backing, thereby facilitating the separation of portions of the bridge member 23" that are located further away from the medial support layer tab. Advantageously, this configuration of the bridge member can prevent unintentional tearing of the dressing support layer and, potentially, separation of the bridge member from the spoke as the dressing support layer is removed from the backing. Also shown in FIG. 16b are bond block zone 45, peripheral support layer tab 28, a visible indicium 61 and a visible indicium 62, all as described above.

Figure 16C:
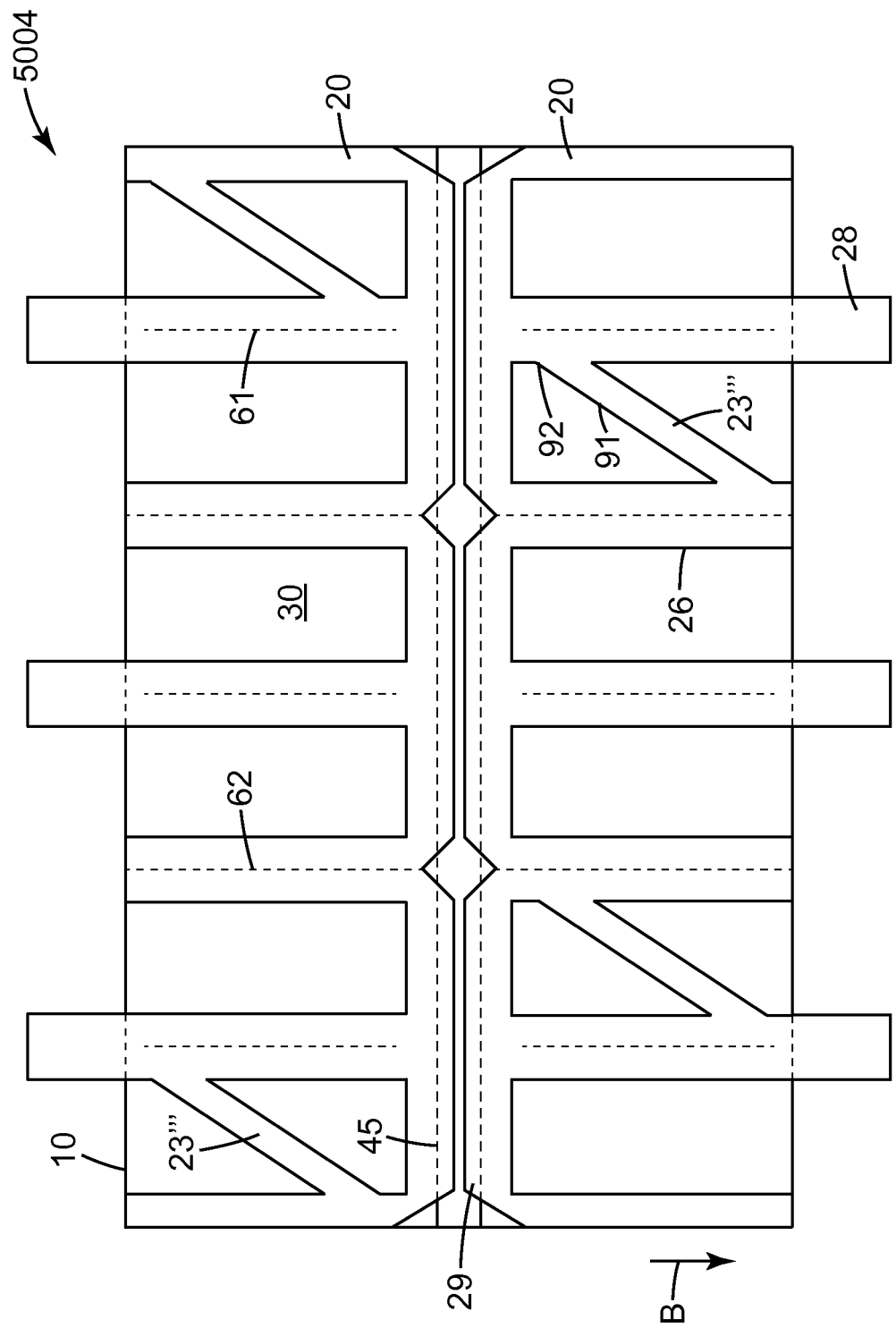

FIG. 16c shows an alternative embodiment (wound dressing system 5004) of the wound dressing system of FIG. 16a with bridge members configured to facilitate removal of the dressing support layer. The bridge members 23''' of the dressing support layer 20 comprise a medial edge 91 proximate the medial portion 22 of the dressing support layer 20. The medial edge 91 comprises at least one closest point 92 that is closer to the medial portion 22 of the dressing support layer 20 than any other point on the medial edge of the bridge member 23'''. The closest point 92 is located where the bridge member 23''' abuts a spoke (e.g., inner spoke 26). Thus, when the medial support layer tab 29 is grasped and lifted away from the backing 30 and/or pulled in the direction of arrow "B", the closest point 92 is the first portion of the bridge member 23''' that is separated from the backing, thereby facilitating the separation of portions of the bridge member 23''' that are located further away from the medial support layer tab. Advantageously, this configuration of the bridge member can prevent unintentional tearing of the dressing support layer and, potentially, separation of the bridge member from the spoke as the dressing support layer is removed from the backing. Also shown in FIG. 16c are bond block zone 45, peripheral support layer tab 28, a visible indicium 61 and a visible indicium 62, all as described above.

In any embodiment of a wound dressing system comprising a bridge member according to the present disclosure, the dressing support layer may comprise a plurality of bridge members, as illustrated in FIGS. 14-16c. In any embodiment, a first bridge member can connect first and second spokes and a second bridge member can connect third and fourth spokes. In any embodiment, the first and second spokes can be disposed on the same section (e.g., the first section) of the dressing support layer as the third and fourth spokes. Alternatively, in any embodiment, the first and second spokes can be disposed on the one section (e.g., the first section) of the dressing support layer and the third and fourth spokes can be disposed on another section (e.g., the second section) of the dressing support layer. In any embodiment at least one of the first, second, third, or fourth spokes can be an outer spoke. In a preferred embodiment (not shown), the bridge members are disposed in an alternating arrangement between the first and second sections as one goes from the first end to the second end of the dressing system.

Figure 17:
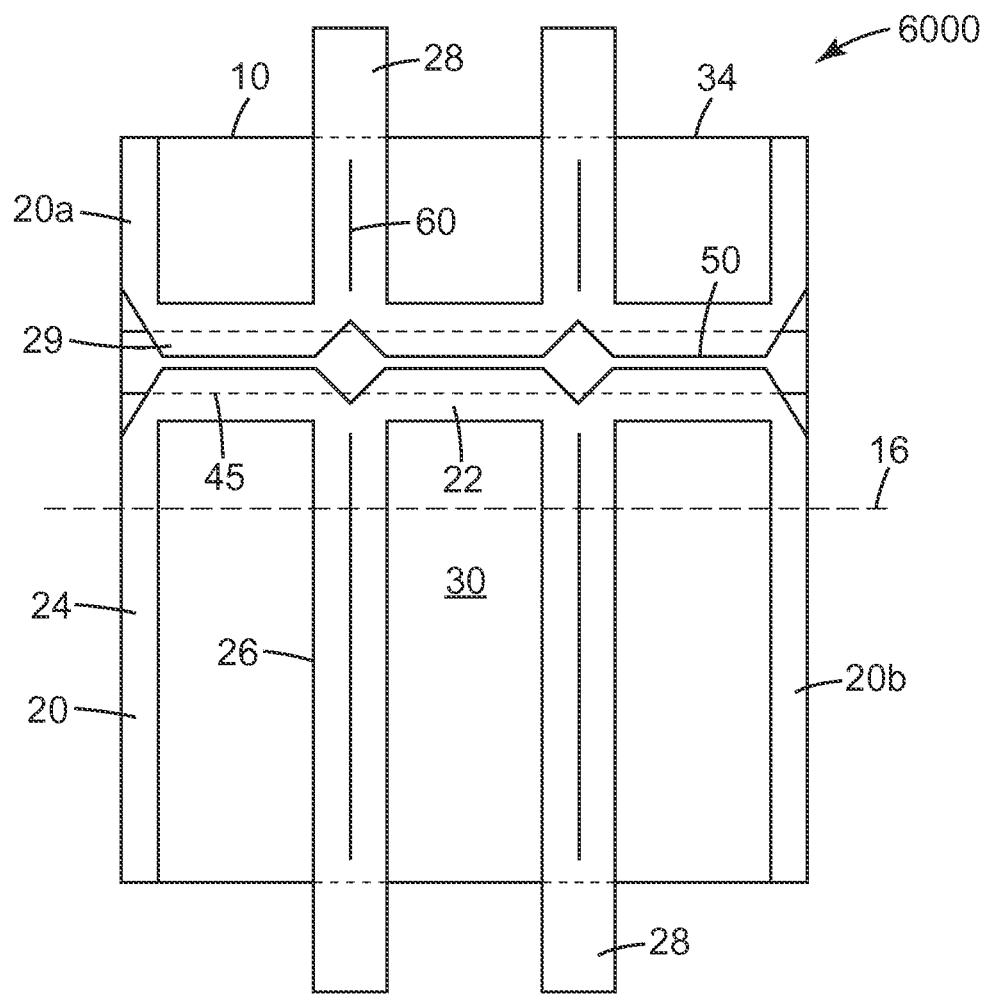
FIG. 17 is a plan view of another alternative embodiment of a wound dressing system according to the present disclosure, wherein the medial portions of the dressing support layer extend substantially parallel to, but are spaced apart from, the central axis of the wound dressing.

Although it may be preferable in some embodiments, it is not required that the gap between the first and second sections of the dressing support layer of a wound dressing system of the present disclosure is coincident, at least in part, with the central axis of the wound dressing. FIG. 17 shows one embodiment of a wound dressing system 6000 wherein the gap 50 between the first section 20a and second section 20b of the dressing support layer 20 is spaced apart from the central axis (i.e., the gap 50 is closer to one lateral edge than the other lateral edge. The wound dressing system 6000 comprises a wound dressing 10 comprising a backing 30 to which the dressing support layer 20 is bonded. Each section (20a and 20b, respectively) of the dressing support layer 20 comprises at least four spokes (i.e., outer spokes 24 and inner spokes 26. The two inner spokes 26 of each section each further comprise a peripheral support layer tab 28, as described herein. In addition, each of the inner spokes 26 comprises a visible indicium 60, which may be an area of weakness, as described herein. The wound dressing system 6000 further comprises a bond-block zone 45, as described herein, which overlaps the gap 50 and the medial portion 22 of the dressing support layer 20, thereby forming a plurality of medial support layer tabs 29.

Similar to other embodiments of the wound dressing system disclosed herein, the wound dressing system 6000 can be cleaved along a line generally defined by the gap 50 to form two cropped wound dressing systems (not shown). In contrast to other wound dressing systems wherein the longitudinal axis 16 is coincident with the central axis and, thus, the longitudinal axis 16 forms an axis of symmetry for the dressing support layer, the two cropped wound dressing systems derived by cleaving the wound dressing system 6000 along a line defined by the gap 50 would not be substantially identical. Advantageously, having the gap 50 between the sections of the dressing support layer eccentric with respect to the central axis provides an alternative point of flexion for the wound dressing system, making it more suitable for particular, relatively large treatment sites (e.g., lower back). In addition, the ability to easily cut the wound dressing system 6000 into two predetermined differently-sized cropped wound dressing systems, each with a plurality of tabs makes the wound dressing system 6000 adaptable to a wide variety of uses.

Wound dressing systems of the present disclosure can be used to cover a treatment site of a patient. In any embodiment, the wound dressing may be disposed in a package (e.g., an individually-wrapped package, a bulk-wrapped package containing a plurality of wound dressing systems) for shipping and storage. During use, the wound dressing system is removed from the package, if present. While grasping at least one of the dressing support layer tabs (e.g., a peripheral support layer tab), the liner, if present, is peeled away from the wound dressing to expose the adhesive on the first side of the backing. Then, while grasping one or more of the tabs (e.g., the peripheral support layer tabs), the wound dressing is positioned over the treatment area and, subsequently, the patient-facing side of the wound dressing is brought into contact with the treatment site, where it is secured via the adhesive on the wound dressing. After securing the wound dressing to the treatment site, each section of the dressing support layer optionally can be removed by grasping at least one of the dressing support layer tabs (e.g., a peripheral support layer tab or a medial support layer tab) and pulling the support layer away from the treatment surface. In a preferred embodiment, the dressing support layer is grasped by a medial support layer tab and the tab is pulled in a direction generally toward a lateral edge of the dressing nearest the medial support layer tab.

As discussed above, a desirable feature of the wound dressing systems of the present disclosure is that they can be cleaved or partially cleaved along predetermined lines that are generally defined, or precisely specified, by the gap between the dressing support layer sections and/or by one or more visible indicia. In some embodiments (e.g., wherein a line defined by the gap or wherein a line defined by a visible indicium if a line of symmetry), cleaving the wound dressing system can yield a plurality of substantially identical cropped wound dressing systems.

Thus, in another aspect, the present disclosure provides a method. The method can be a method of preparing a wound dressing system for application onto a treatment surface (e.g., application to a treatment site as described hereinabove). In a first aspect, the method comprises using any embodiment of the wound dressing system disclosed herein, wherein the wound dressing system comprises a wound dressing having a first end a second end opposite the first end, and a longitudinal axis extending from the first end to the second end; and a dressing support layer. The wound dressing comprises an elastic film backing with an adhesive disposed thereon. The backing comprises a first major surface, a second major surface opposite the first major surface, and a perimeter that includes first and second lateral edges. The lateral edges extend from the first end to the second end. The adhesive is disposed on the first major surface. In any embodiment, the first and second lateral edges can extend substantially parallel to the longitudinal axis. The dressing support layer comprises juxtaposed first and second sections removably mounted on the second major surface of the backing, wherein the juxtaposed first and second sections define a gap between the sections. The gap extends substantially from the first end to the second end. Each section comprises a medial portion extending from about the first end to about the second end, and at least four spokes extending therefrom toward a lateral edge. The at least four spokes comprise a first outer spoke extending substantially to the perimeter at the first end, a second outer spoke extending substantially to the perimeter at the second end, and at least two spaced-apart inner spokes disposed therebetween. At least two of the at least four spokes of each section extend beyond the lateral edge to form peripheral support layer tabs. The dressing support layer defines a plurality of covered portions and uncovered portions of the backing.

The first aspect of the method comprises cleaving the wound dressing along a line substantially defined by the gap between the sections of the dressing support layer to produce a plurality of cropped wound dressing systems, each cropped wound dressing system comprising at least one peripheral support layer tab, and applying a cropped wound dressing of one of the cropped wound dressing systems to a treatment site.

Figure 18:
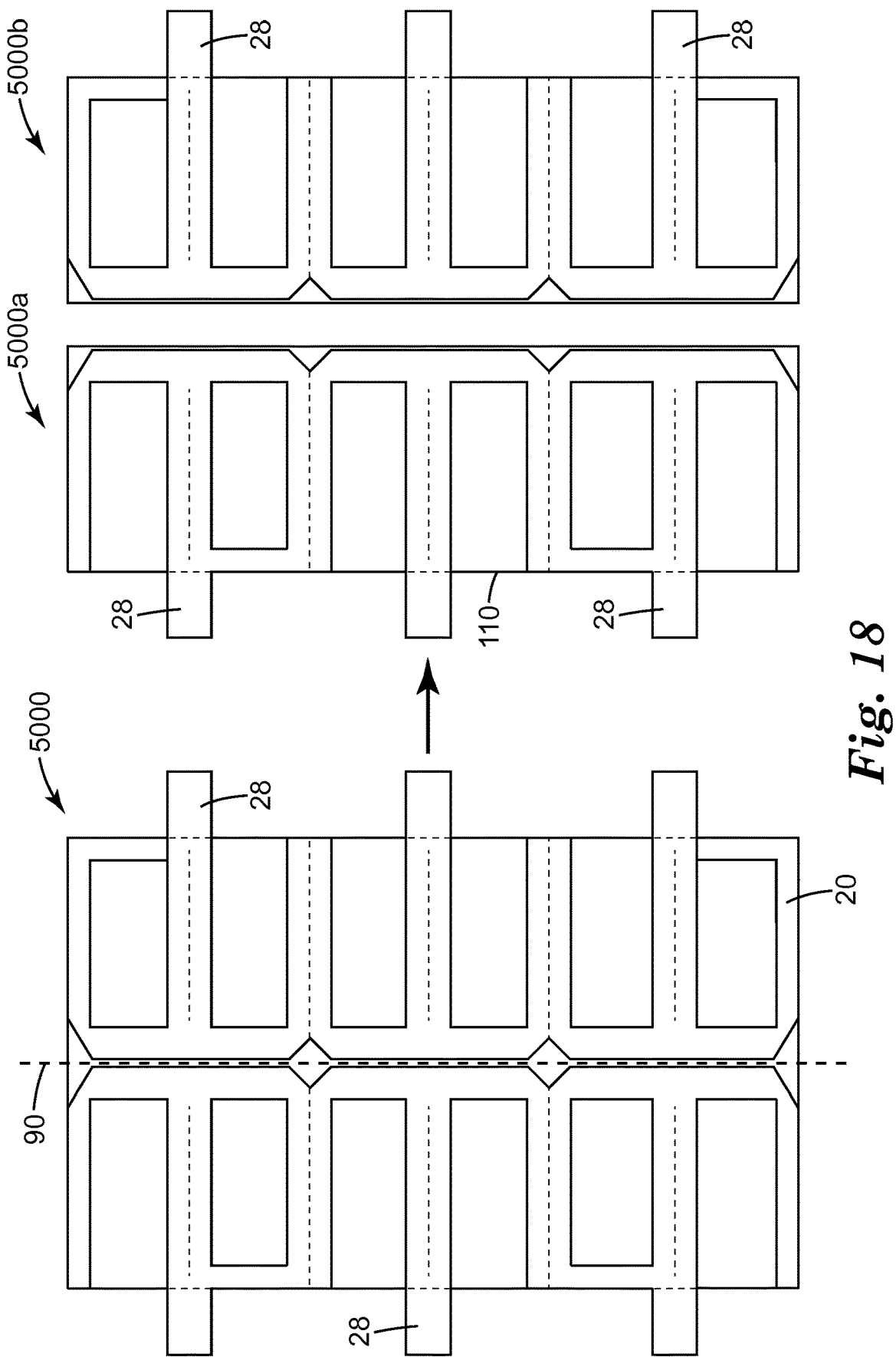
FIG. 18 is a plan view of the wound dressing system of FIG. 14 and two cropped wound dressing systems derived therefrom when the wound dressing system is cleaved along a predetermined path.

FIG. 18 shows the wound dressing system 5000 of FIG. 14 before and after it is cleaved along a predefined line 90 to form a plurality of cropped wound dressing systems (5000a and 5000b, respectively) according to the first aspect of the method. The predefined line 90 is coincident with the gap 50 of the wound dressing system 5000 (see FIG. 14). Because the dressing support layer 20 of the wound dressing system 5000 is asymmetrical with respect to the line 90 of cleavage, the cropped wound dressing systems (5000a and 5000b, respectively), although similar in size and shape, are nonidentical. Each cropped wound dressing system comprises a plurality of peripheral support layer tabs 28, which facilitate the application of the cropped wound dressings 110 of the cropped wound dressing systems to a treatment site. A person having ordinary skill in the art will recognize that this method can be used with any embodiment of a wound dressing system according to the present disclosure.

When the wound dressing system comprises a visible indicium according to the present disclosure, in any embodiment, the method of the first aspect further can comprise cleaving one of the plurality of cropped wound dressing systems along at least one visible indicium to produce a double-cropped wound dressing system, the double-cropped wound dressing system comprising at least one or a portion of one peripheral support layer tab. In these embodiments, applying the wound dressing of one of the cropped wound dressing systems comprises applying a double-cropped wound dressing of one of the double-cropped wound dressing systems.

Figure 19:
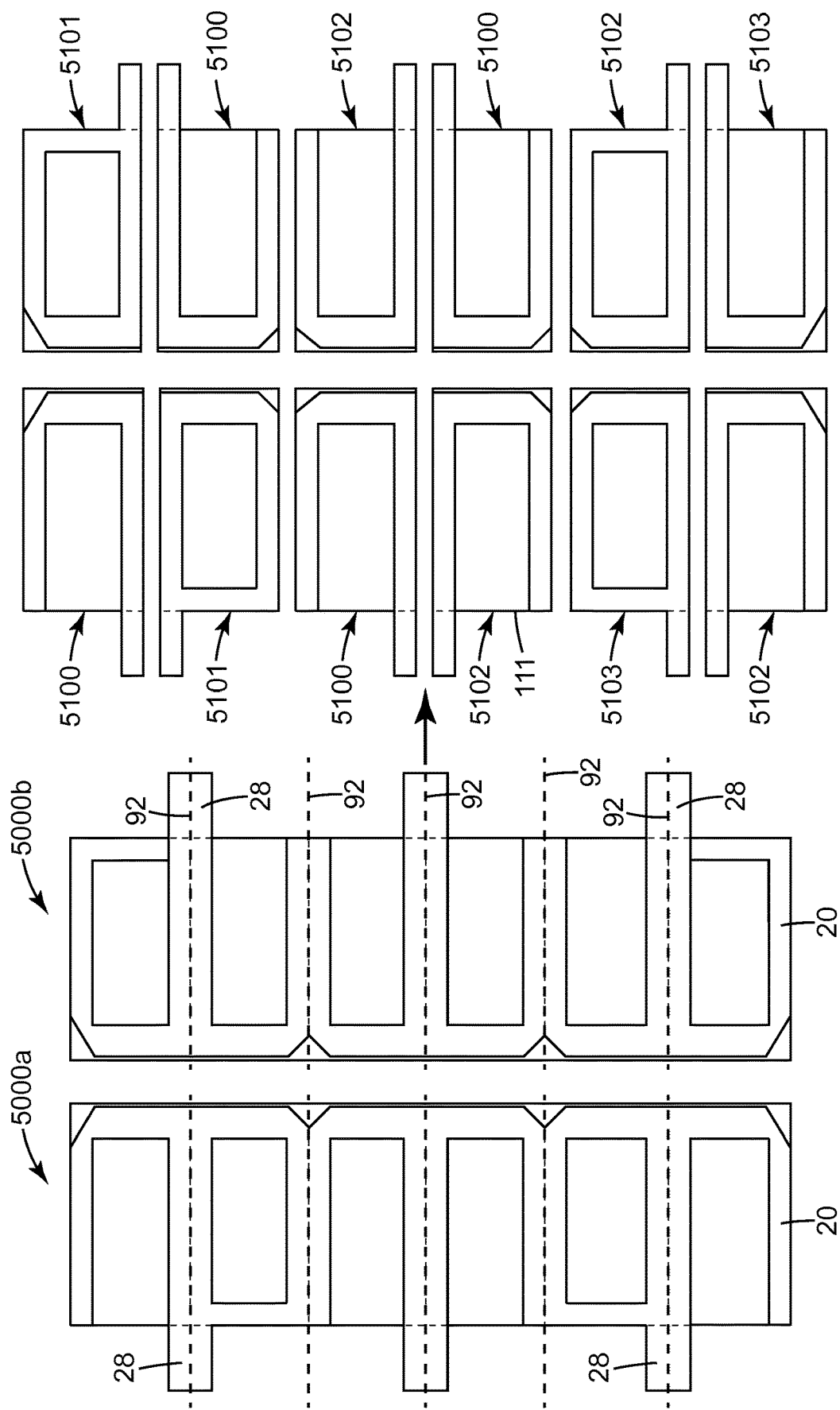
FIG. 19 is a plan view of the cropped wound dressing systems of FIG. 18 and twelve double-cropped wound dressing systems derived therefrom when the cropped wound dressing systems are cleaved along predetermined paths.

FIG. 19 shows the cropped wound dressing systems 5000a and 5000b before and after they are cleaved along predefined lines 92. The predefined lines 92 are coincident with the visible indicia 61 and visible indicia 62 of the wound dressing system 5000 (see FIG. 14). Because the dressing support layer 20 of the cropped wound dressing systems 5000a and 5000b are asymmetrical, the resulting double-cropped wound dressing systems (5100, 5101, 5102, and 5103, respectively, respectively), although similar in size and shape, are nonidentical. Advantageously, each double-cropped wound dressing system comprises at least one portion of peripheral support layer tab 28, which facilitate the application of the double-cropped wound dressings 111 of the double-cropped wound dressing systems to a treatment site. A person having ordinary skill in the art will recognize that this method can be used with any embodiment of a wound dressing system according to the present disclosure.

The second aspect of the method comprises using a wound dressing system according to the present disclosure wherein the wound dressing system comprises at least two visible indicia. The second aspect further comprises cleaving the wound dressing system comprises cleaving the dressing system along any two or more visible indicia to produce a plurality of cropped wound dressing systems, each cropped wound dressing system comprising at least one peripheral support layer tab; and applying a cropped wound dressing of one of the cropped wound dressing systems to a treatment site.

Figure 20:
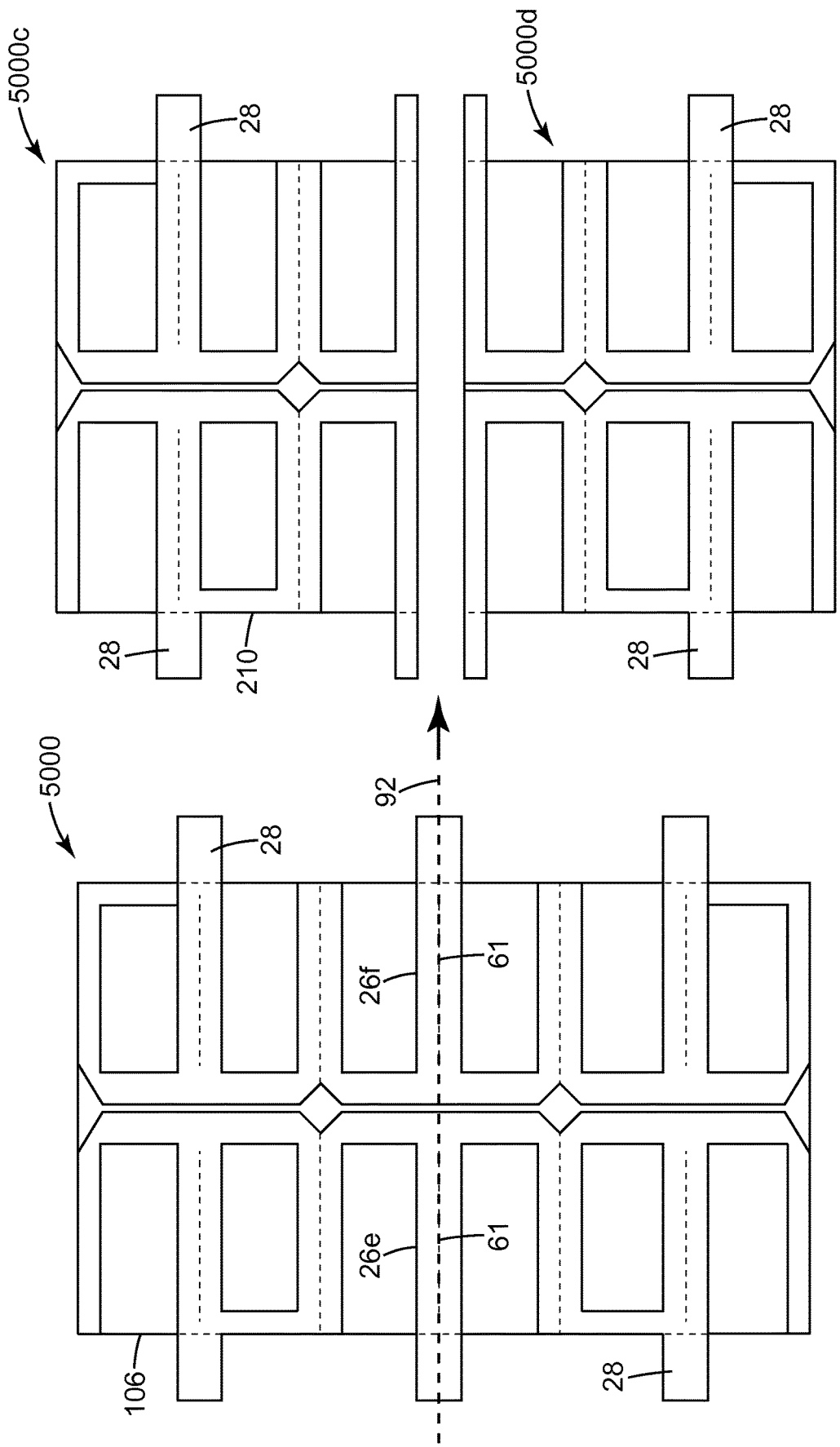
FIG. 20 is a plan view of the wound dressing system of FIG. 14 and two cropped wound dressing systems derived therefrom when the wound dressing system is cleaved along an alternative predetermined path.

FIG. 20 shows the wound dressing system 5000 of FIG. 14 before and after it is cleaved along a predefined line 92 to form a plurality of cropped wound dressing systems (5000c and 5000d, respectively) according to the second aspect of the method. The predefined line 92 is coincident with two visible indicia 61 (i.e., a first visible indicium 61 of inner spoke 26e and a second visible indicium 61 of inner spoke 26f; see also FIG. 14). Because the dressing support layer 20 of the wound dressing system 5000 is asymmetrical with respect to the line 92 of cleavage, the cropped wound dressing systems (5000c and 5000d, respectively), although similar in size and shape, are nonidentical. Each cropped wound dressing system comprises a plurality of peripheral support layer tabs 28, which facilitate the application of the cropped wound dressings 210 of the cropped wound dressing systems to a treatment site. A person having ordinary skill in the art will recognize that this method can be used with any embodiment of a wound dressing system according to the present disclosure wherein the wound dressing system comprises at least two visible indicia.

Another example of the second aspect of the method is illustrated in FIG. 21. The figure shows the wound dressing system 5000 of FIG. 14 before and after it is cleaved along two predefined lines 92 to form a plurality of cropped wound dressing systems (5000*c* and 5000*d*, respectively) according to the second aspect of the method. Each predefined line 92 is coincident with two visible indicia 61 (see also FIG. 14). Because the dressing support layer 20 of the wound dressing system 5000 is asymmetrical with respect to the lines 92 of cleavage, the cropped wound dressing systems (5000*e*, 5000*f,* and 5000*g* respectively), although similar in size and shape, are nonidentical. Each cropped wound dressing system comprises a plurality of peripheral support layer tabs 28, which facilitate the application of the cropped wound dressings 310 of the cropped wound dressing systems to a treatment site. In addition, the support layer of each double cropped wound dressing system is not bonded to the backing along at least a portion of the perimeter of the backing along the four sides/edges of the double cropped wound dressing system.

In any embodiment, the method of the second aspect further can comprise cleaving one of the plurality of cropped wound dressing systems along at least one visible indicium to produce a double-cropped wound dressing system, the double-cropped wound dressing system comprising at least one peripheral support layer tab. In these embodiments, applying the cropped wound dressing of one of the cropped wound dressing systems comprises applying a double-cropped wound dressing of one of the double-cropped wound dressing systems.

Figure 22:
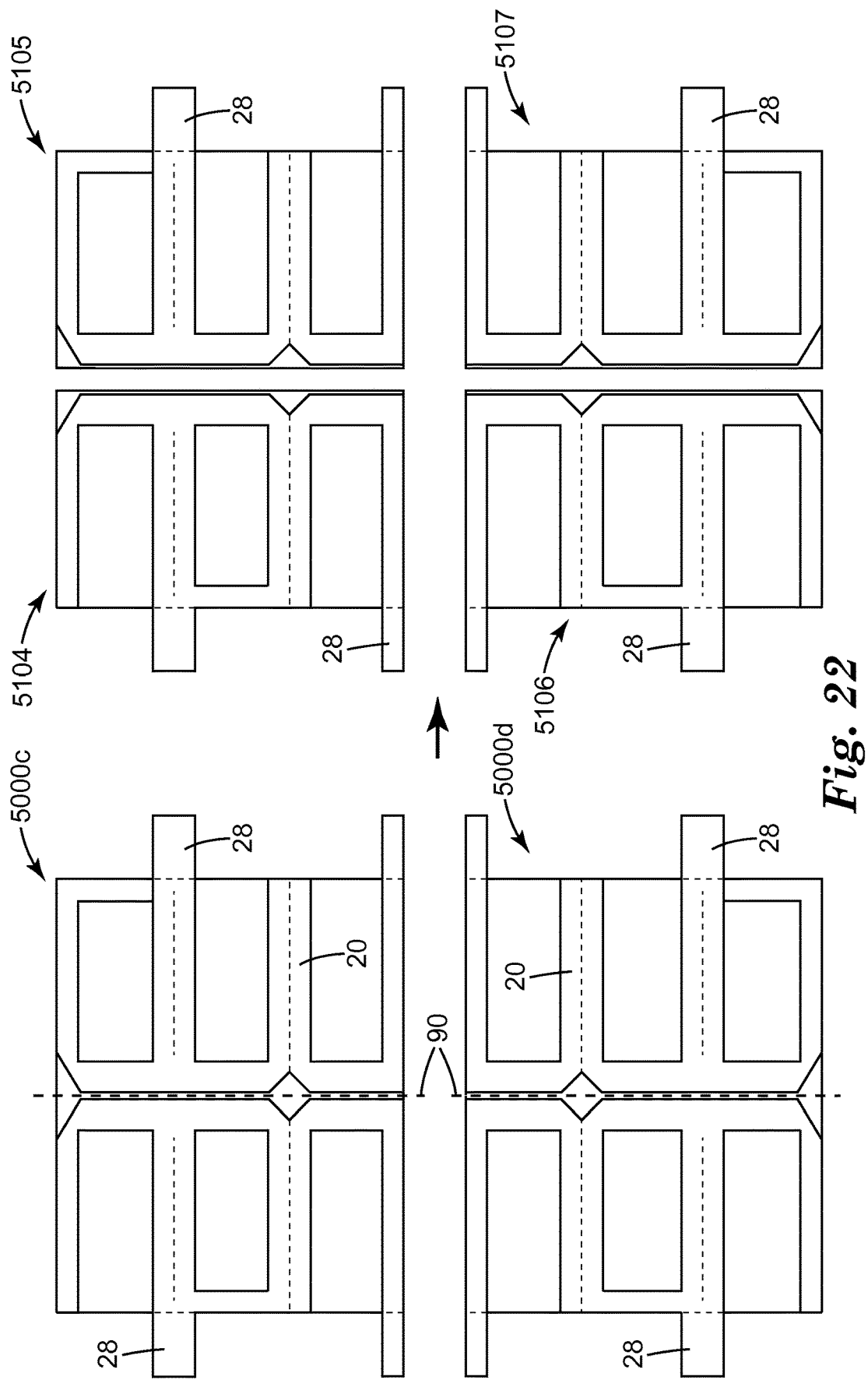
FIG. 22 is a plan view of the cropped wound dressing systems of FIG. 20 and four double-cropped wound dressing systems derived therefrom when the cropped wound dressing systems are cleaved along predetermined paths.

FIG. 22 shows the cropped wound dressing systems 5000*c* and 5000*d* of FIG. 20 before and after they are cleaved along predefined lines 90. The predefined lines 90 are coincident with the gap 50 of the wound dressing system 5000 (see FIG. 14). Because the dressing support layer 20 of the cropped wound dressing systems 5000*c* and 5000*d* are asymmetrical with respect to the predefined lines 90, the resulting double-cropped wound dressing systems (5104, 5105, 5106, and 5107, respectively), although similar in size and shape, are nonidentical. Advantageously, each double-cropped wound dressing system comprises at least one peripheral support layer tab 28, which facilitate the application of the double-cropped wound dressings 211 of the double-cropped wound dressing systems to a treatment site.

Figure 23:
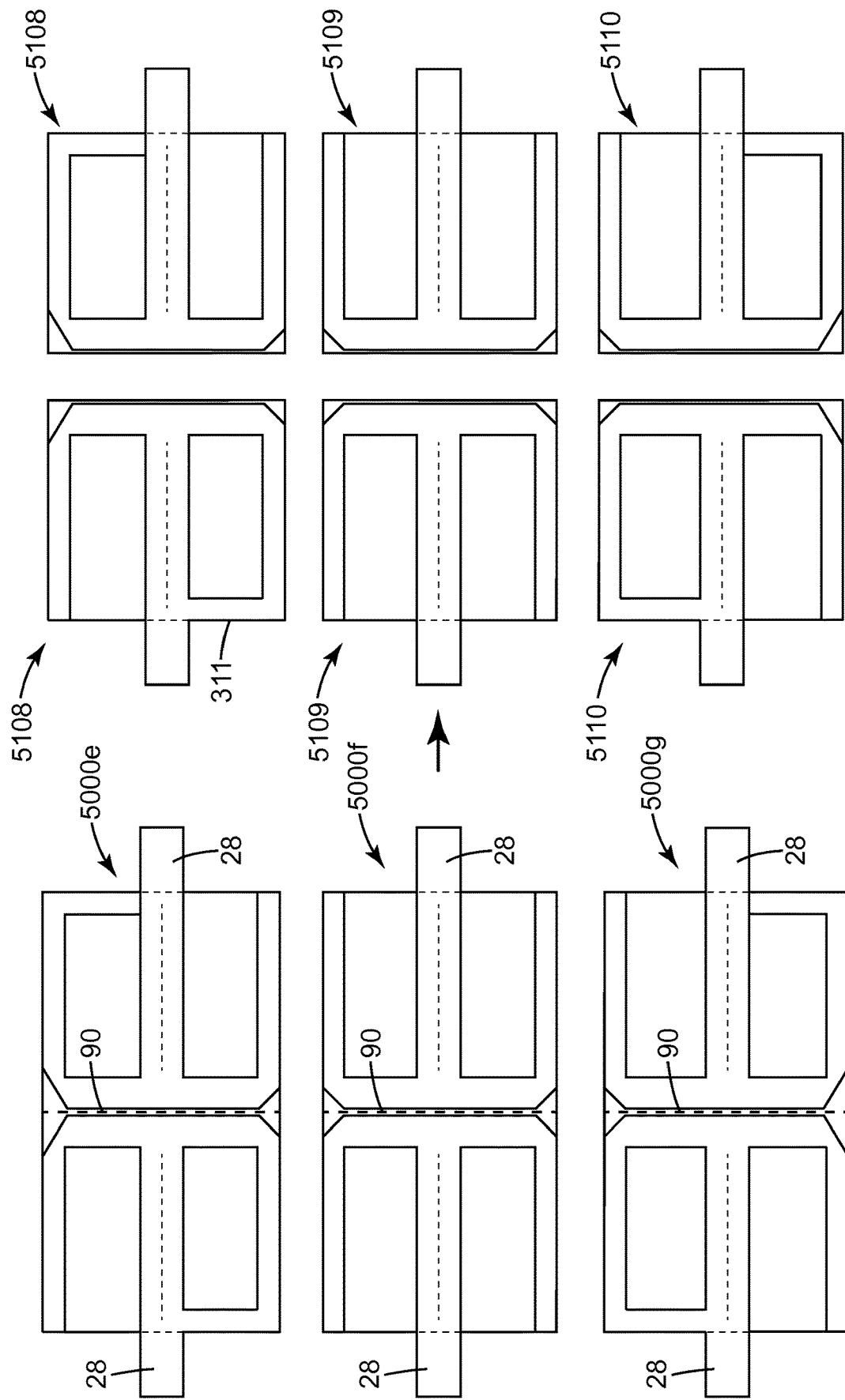
FIG. 23 is a plan view of the cropped wound dressing systems of FIG. 21 and six double-cropped wound dressing systems derived therefrom when the cropped wound dressing systems are cleaved along predetermined paths.

FIG. 23 shows the cropped wound dressing systems 5000*e* and 5000*f* of FIG. 21 before and after they are cleaved along predefined lines 90. The predefined lines 90 are coincident with the gap 50 of the wound dressing system 5000 (see FIG. 14). Because the dressing support layer of each of the cropped wound dressing systems 5000*e*, 5000*f,* and 5000*g* are symmetrical with respect to the predefined lines 90 but are nonidentical, the resulting double-cropped wound dressing systems (5108, 5109, and 5110, respectively), although similar in size and shape, are nonidentical. Advantageously, each double-cropped wound dressing system comprises at least one peripheral support layer tab 28, which facilitate the application of the double-cropped wound dressings 311 of the double-cropped wound dressing systems to a treatment site. In addition, the support layer of each double cropped wound dressing system is not bonded to the backing along at least a portion of the perimeter of the backing along the four distinct sides/edges of the double cropped wound dressing system.

Figure 24:
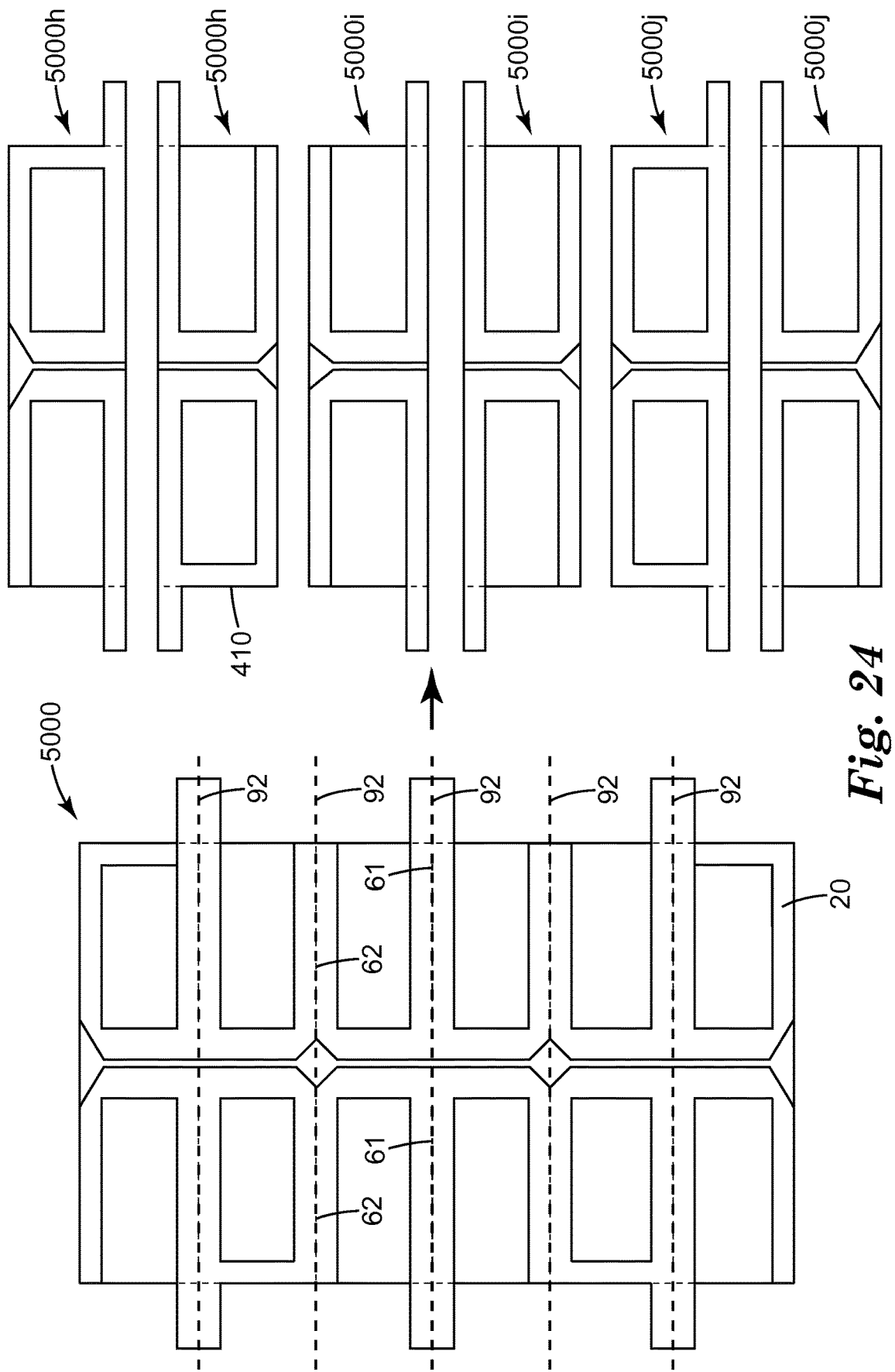
FIG. 24 is a plan view of the wound dressing system of FIG. 14 and six cropped wound dressing systems derived therefrom when the wound dressing system is cleaved along five predetermined paths.

FIG. 24 shows the wound dressing system 5000 of FIG. 14 before and after it is cleaved along a plurality of predefined lines 92 to form a plurality of cropped wound dressing systems (5000*h*, 5000*i*, and 5000*j*, respectively) according to the second aspect of the method. The predefined lines 92 are coincident with two visible indicia 61 or two visible indicia 62, see FIG. 14). Because the dressing support layer 20 of the wound dressing system 5000 is asymmetrical with respect to the lines 92 of cleavage, the cropped wound dressing systems (5000*h*, 5000*i*, and 5000*j*, respectively), although similar in size and shape, are nonidentical. Each cropped wound dressing system comprises a plurality of peripheral support layer tabs 28, which facilitate the application of the cropped wound dressings 410 of the cropped wound dressing systems to a treatment site. In addition, the support layer of each cropped wound dressing system is not bonded to the backing along at least a portion of the perimeter of the backing along two sides/edges of the cropped wound dressing system. If a bond block material is used along the gap area (not shown), then the support layer is not bonded to three sides/edges of the backing along the perimeter of the backing f the cropped wound dressing system.

Figure 25:
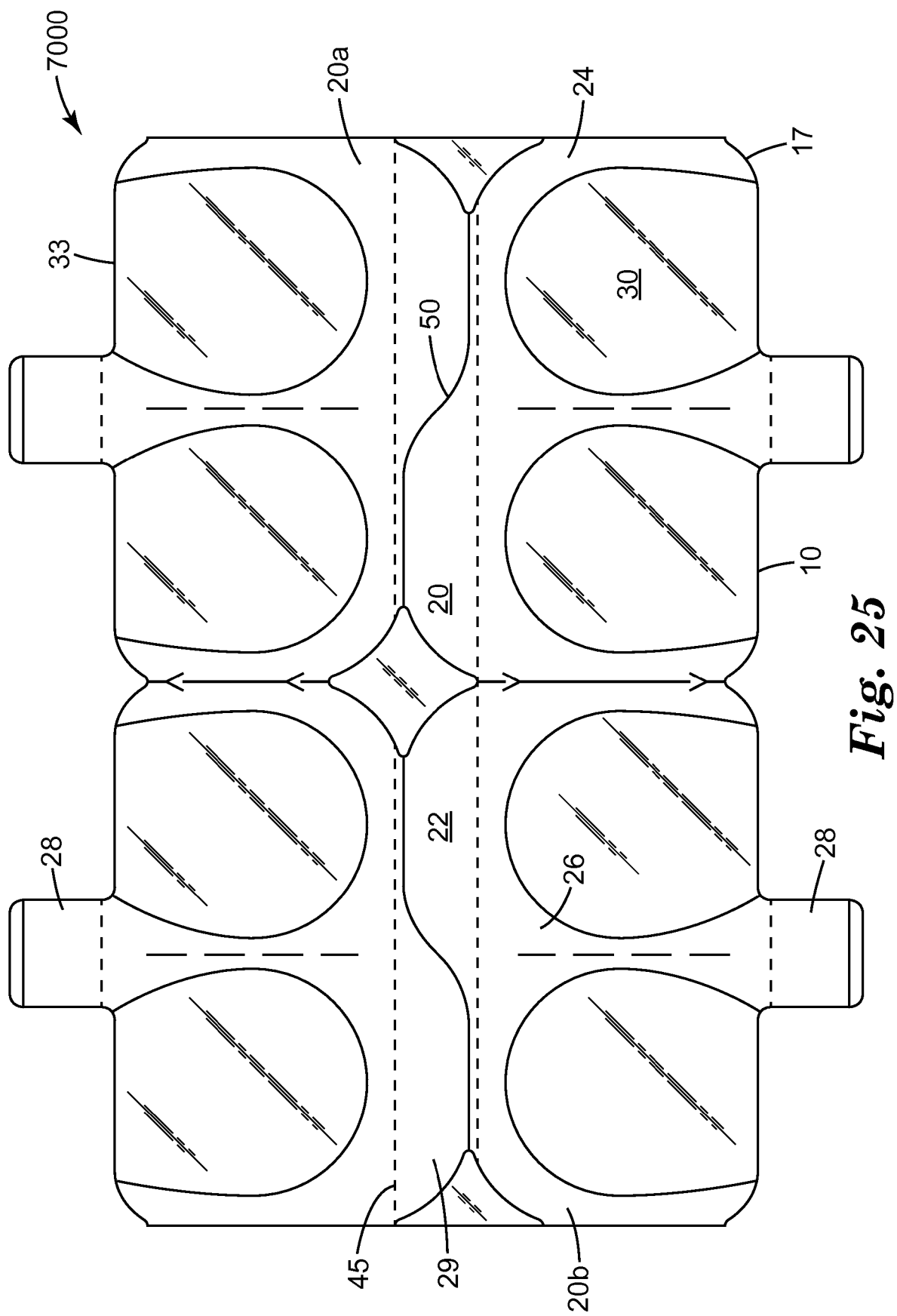
FIG. 25 is a plan view of another alternative embodiment of a wound dressing system according to the present disclosure.

In any embodiment, a wound dressing system of the present disclosure optionally may comprise a wound dressing having at least one radiused (e.g., rounded) corner. FIG. 25 shows one embodiment of a wound dressing system 7000 comprising a wound dressing 10 comprising a backing 30 with at least one radiused corner 17. The wound dressing system 7000 further comprises a dressing support layer 20 comprising juxtaposed first section 20*a* and second section 20*b* as described herein. Each section of the dressing support layer 20 comprises a medial portion 22 from which at least four spokes (e.g., outer spokes 24 and inner spokes 26) extend toward a lateral edge, as described above. At least two of the spokes of each section of the dressing support layer 20 extends beyond a lateral edge of the backing 30 to form a peripheral support tab 28. Disposed at the junction of the first and section sections 20*a* and 20*b* of the dressing support layer is a gap 50, as described herein. The wound dressing system 7000 further comprises optional bond block zone 45 as described herein, which forms the medial support layer tabs 29, as described herein. As shown in FIG. 25, the lateral edges of the backing do not necessarily have to be straight.

In any embodiment, a wound dressing system of the present disclosure optionally may comprise a dressing support layer 20 that comprises at least one spoke (e.g., inner spoke 26) that has a width dimension that broadens proximate the medial portion 22 of the dressing support layer 20 and/or broadens proximate the perimeter 33 of the wound dressing 10, as shown in the wound dressing system 7000 of FIG. 25. Advantageously, this configuration provides more support to the perimeter 33 and central region of the backing 30 of the wound dressing 10 during application. In addition, the narrow portion of the spoke provides more uncovered backing 30, thereby providing better conformability and visibility of the treatment area when applying the wound dressing 10.

In any embodiment, a wound dressing system of the present disclosure optionally may comprise a curvilinear gap 50, as shown in the wound dressing system 7000 of FIG. 25. For example, the gap 50 may define one or more S-shapes (as shown in FIG. 25), or it may take the form of a crenate, crenellated, or scalloped edge. The curvilinear forms may provide a substantially longer gap 50, relative to the length of the wound dressing 10, making it significantly easier for the user to locate and grasp a medial support layer tab when applying the dressing to a treatment site.

Preferably, the absorbent pad 80, if present in a wound dressing system of the present disclosure comprises a nonwoven, a foam, a hydrocolloid or a hydrogel pad. In any embodiment of a wound dressing system of the present disclosure, the backing 30 can comprise a transparent elastic polymeric film (e.g., urethane) having a thickness no greater than 0.15 mm (e.g., most preferably 0.015-0.100 mm) It will be appreciated that, in an embodiment comprising the absorbent pad 80, the pad is much thicker, stiffer and heavier than the film backing 30.

The described embodiments are illustrative examples, and the features of one embodiment may be used in connection with the other embodiments. For example, a bridge member could be added to the wound dressing system 1000 embodiment of FIGS. 1-4.

Backing Materials

Suitable backings 30 include, for example, nonwoven fibrous webs, woven fibrous webs, knits, films and other familiar backing materials. The preferred backing materials are translucent or transparent polymeric elastic films. Most preferably, the backing is a high moisture vapor permeable film backings. U.S. Pat. No. 3,645,835, the disclosure of which is hereby incorporated by reference, describes methods of making such films and methods for testing their permeability.

Preferably, the film/adhesive composite should transmit moisture vapor at a rate equal to or greater than human skin. Preferably, the adhesive coated film transmits moisture vapor at a rate of at least 300 g/m2/24 hrs/37° C./100-10% RH, more preferably at least 700 g/m2/24 hrs/37° C./100-10% RH, and most preferably at least 2000 g/m2/24 hrs/37° C./100-10% RH using the inverted cup method.

The backing is preferably conformable to anatomical surfaces. As such, when the backing is applied to an anatomical surface, it conforms to the surface even when the surface is moved. The preferred backing is also conformable to animal anatomical joints. When the joint is flexed and then returned to its unflexed position, the backing stretches to accommodate the flexion of the joint, but is resilient enough to continue to conform to the joint when the joint is returned to its unflexed condition. Preferably, the backing has an ultimate elongation of greater than 200%. More preferably, the backing has an ultimate elongation of greater than 400%.

A description of this characteristic of backings preferred for use with the wound dressing systems of the present disclosure can be found in issued U.S. Pat. Nos. 5,088,483 and 5,160,315, the disclosures of which are hereby incorporated by reference in their entirety. Particularly preferred backings are elastomeric polyurethane, co-polyester, or polyether block amide films. These films combine the desirable properties of resiliency, high moisture vapor permeability, and transparency found in preferred backings.

Adhesive

While any pressure sensitive adhesive can be used for adhesive 40, preferred adhesives include a pressure sensitive adhesive that is reasonably skin compatible, such as soft silicone adhesives, Kraton based adhesive, hydrocolloid adhesives, or the acrylate copolymers described in U.S. Pat. No. RE 24,906, the disclosure of which is hereby incorporated by reference in its entirety. Particularly preferred is a 97:3 iso-octyl acrylate:acrylamide copolymer. Also preferred is an 70:15:15 isooctyl acrylate:ethyleneoxide acrylate:acrylic acid terpolymer, as described in U.S. Pat. No. 4,737,410 (Example 31), the disclosure of which is hereby incorporated by reference in its entirety. Other useful adhesives are described in U.S. Pat. Nos. 3,389,827, 4,112,213, 4,310,509, and 4,323,557, the disclosures of which are hereby incorporated by reference in their entirety. Inclusion of medicaments or antimicrobial agents in the adhesive is also contemplated, as described in U.S. Pat. Nos. 4,310,509 and 4,323,557 both of which are hereby incorporated by reference in their entirety.

The preferred pressure sensitive adhesives described above preferably transmit moisture vapor at rate greater to or equal to that of human skin. While such a characteristic can be achieved through the selection of an appropriate adhesive or through use of a nonwoven (e.g., melt blown) adhesive (as described in U.S. Pat. Nos. 6,171,985, 6,368,687, and PCT Publication No. WO 99/27975 (all of which are incorporated herein by reference in their entirety)), it is also contemplated in the present invention that other methods of achieving a high relative rate of moisture vapor transmission may be used, such as pattern coating the adhesive on the backing.

Absorbent Pad Materials

Absorbent pad 80 can be manufactured of any of a variety of materials including, but not limited to, foams, gels, hydrocolloids, wovens or nonwovens. Absorbent pad 80 is useful for containing a number of substances, including antimicrobial agents, drugs for transdermal drug delivery, chemical indicators to monitor hormones or other substances in a patient, etc.

The preferred island pad providing an absorbent matrix includes the normal adhesives which are applied to the skin, or the hydrocolloid compositions described in U.S. Pat. Nos. 5,622,711 and 5,633,010, the disclosure of which is hereby incorporated by reference in their entirety. The hydrocolloid absorbent may comprise, for example, a natural hydrocolloid, such as pectin, gelatin, or carboxymethylcellulose (CMC) (Aqualon Corp., Wilmington, Del.), a semi-synthetic hydrocolloid, such as cross-linked carboxymethylcellulose (x-link CMC) (e.g. Ac-Di-Sol; FMC Corp., Philadelphia, Pa.), a synthetic hydrocolloid, such as cross-linked polyacrylic acid (PAA) (e.g., CARBOPOL No. 974P; B.F. Goodrich, Brecksville, Ohio), or a combination thereof. Preferably, the hydrocolloid absorbent component comprises from about 5 percent to about 60 percent by weight of the adhesive composition. When preparing anti adhesive composition for use in a wound dressing the hydrocolloid absorbent preferably comprises from about 20 percent to about 40 percent by weight of the composition.

Release Liner Materials

Release Liner 90 can be made of Kraft papers, polyethylene, polypropylene, polyester or composites of any of these materials. The liners are preferably coated with release agents such as fluorochemicals or silicones. For example, U.S. Pat. No. 4,472,480, the disclosure of which is hereby incorporated by reference in its entirety, describes low surface energy perfluorochemical liners. The preferred liners are papers, polyolefin films, or polyester films coated with silicone release materials. Examples of commercially available silicone coated release papers are silicone release papers available from Loparex (Cary, N.C.) or silicone coated poly films available from Huhtamaki (Forchheim, Germany)

Other combinations of adhesives and liners are contemplated for use with embodiments according to the present invention. Those skilled in the art will be familiar with the processes of testing a new adhesive against different liners or a new liner against different adhesives to arrive at the combination of qualities desired in a final product. The considerations pertinent to the selection of a silicone release liner can be found in Chapter 18 of the Handbook of Pressure Sensitive Adhesive Technology, Van Nostrand-Reinhold, 1982, pp. 384-403. U.S. Pat. No. 4,472,480 also describes considerations pertinent to the selection of a perfluoropolyether release liner.

Liners are available from a variety of manufacturers in a wide variety of proprietary formulations. Those skilled in the art will normally test those liners in simulated use conditions against an adhesive of choice to arrive at a product with the desired release characteristics.

Dressing Support Layer Materials

The preferred dressing support layer material used to supply the dressing support layer 20 and sections thereof is preferably substantially more rigid than the backing 30 to prevent the backing from wrinkling during application. The dressing support layer material can be heat-sealable to the backing 30, with or without the low adhesion coating described above. In general, the preferred dressing support layer materials include, but are not limited to, polyethylene/ vinyl acetate copolymer-coated papers and polyester films. One example of a preferred carrier material is a polyethylene/vinyl acetate copolymer coated super calendared Kraft paper available from Loparex (Cary, N.C.).

Exemplary Embodiments

Embodiment A is a wound dressing system, comprising:
a wound dressing having a first end a second end opposite the first end, and a longitudinal axis extending from the first end to the second end; the wound dressing comprising:
an elastic film backing, the backing comprising a first major surface, a second major surface opposite the first major surface, and a perimeter that includes first and second lateral edges, the lateral edges extending from the first end to the second end;
an adhesive disposed on the first major surface; and
a dressing support layer comprising juxtaposed first and second sections removably mounted on the second major surface of the backing, wherein the juxtaposed first and second sections define a gap between the sections, wherein the gap extends substantially from the first end to the second end;
wherein each section comprises a medial portion extending from about the first end to about the second end, and at least four spokes extending therefrom toward a lateral edge, wherein the at least four spokes comprise a first outer spoke extending substantially to the perimeter at the first end, a second outer spoke extending substantially to the perimeter at the second end, and at least two spaced-apart inner spokes disposed therebetween;
wherein at least two of the at least four spokes of each section extend beyond the lateral edge to form peripheral support layer tabs;
wherein the dressing support layer defines a plurality of covered portions and uncovered portions of the backing.

Embodiment B is the wound dressing system of Embodiment A, wherein the wound dressing comprises a central axis extending from the first end to the second end.

Embodiment C is the wound dressing of Embodiment A or Embodiment B, wherein the first and second lateral edges extend substantially parallel to the longitudinal axis.

Embodiment D is the wound dressing system of any one of the preceding Embodiments, wherein the plurality of uncovered portions including at least two uncovered portions along the first lateral edge and at least two uncovered portions along the second lateral edge.

Embodiment E is the wound dressing of any one of the preceding Embodiments, wherein at least one outer spoke of at least one section of the dressing support layer extends along a portion of the first lateral edge or the second lateral edge.

Embodiment F is the wound dressing system of any one of the preceding Embodiments, The wound dressing system of any one of the preceding claims, wherein at least one of the inner spokes of the first section extends toward the first lateral edge substantially opposite one of the inner spokes of the second section.

Embodiment G is the wound dressing of Embodiment F, wherein each of a plurality of inner spokes of the first section extends toward the first lateral edge substantially opposite one of the inner spokes of the second section.

Embodiment H is the wound dressing system of any one of the preceding Embodiments, wherein the first outer spoke of at least one of the sections extends along a portion of the perimeter of the backing at the first end and/or at the second end.

Embodiment I is the wound dressing system of Embodiment H, wherein the first outer spoke extends along at least 20 percent of the perimeter at the first end and/or the second outer spoke extends along at least 20 percent of the perimeter at the second end.

Embodiment J is the wound dressing system of any one of the preceding Embodiments, wherein the outer spoke of the first section, at the first end of the wound dressing, comprises a peripheral support layer tab; wherein each of the other spokes of the first section, in order from the first end to the second end, alternate between a spoke not having a peripheral support layer tab and a spoke having a peripheral support layer tab.

Embodiment K is the wound dressing system of any one of the preceding Embodiments, wherein the outer spoke of the second section, at the first end of the dressing, comprises a peripheral support layer tab; wherein each of the other spokes of the second section, in order from the first end to the second end, alternate between a spoke not having a peripheral support layer tab and a spoke having a peripheral support layer tab.

Embodiment L is the wound dressing system of any one of Embodiments A through I, wherein the outer spoke of the first section, at the first end of the wound dressing, does not comprise a peripheral support layer tab; wherein each of the other spokes of the first section, in order from the first end to the second end, alternate between a spoke having a peripheral support layer tab and a spoke not having a peripheral support layer tab.

Embodiment M is the wound dressing system of any one of Embodiments A through I, wherein the outer spoke of the second section, at the first end of the wound dressing, comprises a peripheral support layer tab; wherein each of the other spokes of the second section, in order from the first end to the second end, alternate between a spoke not having a peripheral support layer tab and a spoke having a peripheral support layer tab.

Embodiment N is the wound dressing system of any one of Embodiments A through I, wherein each of the inner and outer spokes comprises a peripheral support layer tab.

Embodiment O is the wound dressing system of any one of the preceding Embodiments, wherein each section of the dressing support layer comprises three inner spokes.

Embodiment P is the wound dressing system of any one of the preceding Embodiments, wherein each section of the dressing support layer comprises five inner spokes.

Embodiment Q is the wound dressing system of any one of the preceding Embodiments, wherein at least one of the inner spokes of each section extends substantially along a line that is perpendicular to the longitudinal axis.

Embodiment R is the wound dressing system of any one of the preceding Embodiments, wherein a plurality of inner spokes of each section extend along lines that are each substantially perpendicular to the longitudinal axis.

Embodiment S is the wound dressing system of Embodiment F or any dependent Embodiment thereof, wherein at least one of the inner spokes of the first section and a corresponding inner spoke opposite thereof in the second section each comprises a visible indicium.

Embodiment T is the wound dressing system of Embodiment S, wherein each of the inner spokes comprises a visible indicium.

Embodiment U is the wound dressing system of Embodiment S or Embodiment T, wherein each of the visible indicia forms a line extending along the spoke, wherein a first line extends along a longitudinal axis of the at least one of the inner spokes of the first section and a second line extends along a longitudinal axis of the corresponding inner spoke opposite thereof in the second section.

Embodiment V is the wound dressing system of any one of Embodiments S through U, wherein the visible indicia comprise an area of weakness of the dressing support layer, the area of weakness defining a portion of the dressing support layer that facilitates folding the wound dressing along a predefined path.

Embodiment W is the wound dressing system of any one of any one of the preceding Embodiments, wherein the plurality of uncovered portions includes an uncovered portion along the perimeter at first end or at the second end.

Embodiment X is the wound dressing system of any one of the preceding Embodiments, wherein the plurality of uncovered portions includes an uncovered portion that forms a part of the gap.

Embodiment Y is the wound dressing system of any one of the preceding Embodiments, wherein the dressing support layer comprises a bridge member overlapping the backing and spaced apart from the medial portion, the bridge member connecting a first spoke to a second spoke adjacent the first spoke; wherein the first spoke, the second spoke, the medial portion, and the bridge member define an uncovered portion of the backing.

Embodiment Z is the wound dressing system of Embodiment Y, wherein the bridge member comprises an medial edge proximate the medial portion from which the adjacent spokes extend, wherein a closest point of the medial edge proximate the first spoke is closer to the medial portion of the dressing support layer than any other point on the medial edge, wherein the closest point abuts one of the adjacent spokes.

Embodiment AA is the wound dressing system of Embodiment Y or Embodiment Z, wherein the bridge member extends along at least a portion of the first or second lateral edge.

Embodiment BB is the wound dressing system of Embodiment AA, wherein at least part of the bridge member extends laterally beyond the portion of the first or second lateral edge.)

Embodiment CC is the wound dressing system of Embodiment BB, wherein the part of the bridge member extending beyond the first or second lateral edge is connected to a peripheral support layer tab.

Embodiment DD is the wound dressing system of any one of Embodiments Y through CC, wherein the dressing comprises a plurality of bridge members, a first bridge member connecting the first and second spokes and a second bridge member connecting a third spoke adjacent a fourth spoke.

Embodiment EE is the wound dressing system of Embodiment DD, wherein the first section of the dressing support layer comprises the first and second spokes and the second section of the dressing support layer comprises the third and fourth spokes.

Embodiment FF is the wound dressing system of Embodiment DD or Embodiment EE, wherein at least one of the first, second, third, or fourth spokes is an outer spoke.

Embodiment GG is the wound dressing system of Embodiment S or any dependent Embodiment thereof:
wherein the dressing support layer comprises a first inner spoke of the first section and a second inner spoke of the second section;
wherein both the first inner spoke and second inner spoke comprise lines of indicia;
wherein the first inner spoke extends away from the longitudinal axis opposite the second inner spoke;
wherein cutting the system along a line defined by the lines of indicia creates two smaller wound dressing systems of approximately equal size.

Embodiment HH is the wound dressing system of any one of the preceding Embodiments, further comprising a liner releasably adhered to the adhesive.

Embodiment II is the wound dressing system of Embodiment HH, wherein the liner comprises at least two separate parts.

Embodiment JJ is the wound dressing system of Embodiment HH or Embodiment II, wherein the liner further comprises at least one liner tab that extends beyond the peripheral edge of the backing.

Embodiment KK is the wound dressing system of any one of Embodiments HH through JJ, wherein at least a portion of the at least one liner tab overlaps a peripheral support layer tab.

Embodiment LL is the wound dressing system of any one of the preceding Embodiments, further comprising a bond-block zone on the second major surface of the backing, wherein the support layer is not bonded to the second major surface of the backing in the bond-block zone.

Embodiment MM is the wound dressing system of Embodiment LL, wherein a portion the gap overlaps the bond-block zone.

Embodiment NN is the wound dressing system of Embodiment MM, wherein the entire gap overlaps the bond-block zone.

Embodiment OO is the wound dressing system of Embodiment MM or Embodiment NN, wherein a portion of the dressing support layer that overlaps the bond-block zone proximate the gap forms a medial support layer tab.

Embodiment PP is the wound dressing system of any one of Embodiments MM through OO, as dependent on Embodiment B, wherein the bond-block zone is disposed proximate the central axis.

Embodiment QQ is the wound dressing system of any one of Embodiments B through PP, wherein the central axis forms a line of symmetry for dressing support layer.

Embodiment RR is the wound dressing system of any one of the preceding Embodiments, wherein at least one corner of the backing defines a curve.

Embodiment SS is a method, comprising:

cleaving the wound dressing system of any one of the preceding Embodiments, wherein cleaving the wound dressing system comprises cleaving the wound dressing along a line substantially defined by the gap to produce a plurality of cropped wound dressing systems, each cropped wound dressing system comprising a cropped wound dressing and at least one peripheral support layer tab; and applying the cropped wound dressing of one of the cropped wound dressing systems to a treatment site.

Embodiment TT is the method of Embodiment SS as dependent upon Embodiment S or any dependent Embodiment thereof, further comprising cleaving one of the plurality of cropped wound dressing systems along at least one visible indicium to produce a double-cropped wound dressing system, the double-cropped wound dressing system comprising a double-cropped wound dressing and at least one peripheral support layer tab, wherein applying the cropped wound dressing of one of the cropped wound dressing systems comprises applying the double-cropped wound dressing of one of the double-cropped wound dressing systems.

Embodiment UU is a method, comprising:

cleaving the wound dressing of Embodiment S or any dependent Embodiment thereof, wherein cleaving the wound dressing comprises cleaving the dressing along any two or more visible indicia to produce a plurality of cropped wound dressing systems, each cropped wound dressing system comprising a cropped wound dressing and at least one peripheral support layer tab; and applying the cropped wound dressing of one of the cropped wound dressing systems to a treatment site.

Embodiment VV is the method of Embodiment UU, further comprising cleaving one of the plurality of cropped wound dressing systems along a line substantially defined by the gap to produce a plurality of double-cropped wound dressing systems, each double-cropped wound dressing system comprising a double cropped wound dressing and at least one peripheral support layer tab, wherein applying the cropped wound dressing of one of the cropped wound dressing systems comprises applying the double-cropped wound dressing of one of the double-cropped wound dressing systems.

Embodiment WW is a wound dressing system, comprising:

a wound dressing having a first end a second end opposite the first end, and a longitudinal axis extending from the first end to the second end; the wound dressing comprising:

an elastic film backing, the backing comprising a first major surface, a second major surface opposite the first major surface, and a perimeter that includes first and second lateral edges, the lateral edges extending from the first end to the second end;

an adhesive disposed on the first major surface; and a dressing support layer comprising a plurality of sections including juxtaposed first and second sections removably mounted on the second major surface of the backing layer, wherein the juxtaposed first and second sections define a gap extending substantially from the first end to the second end;

wherein the first and second sections each comprise a medial portion extending from about the first end to about the second end;

wherein the dressing support layer comprises at least four spokes extending toward a first lateral edge from a first medial portion proximate the first lateral edge and at least four spokes extending toward a second lateral edge from a second medial portion proximate the second lateral edge;

wherein each of the at least four spokes comprise a first outer spoke extending to the perimeter at the first end, a second outer spoke extending to the perimeter at the second end, and at least two spaced-apart inner spokes disposed therebetween;

wherein at least two of each of the at least four spokes extend beyond the lateral edge to form peripheral support layer tabs;

wherein the dressing support layer defines a plurality of covered portions and uncovered portions of the backing layer.

Embodiment XX is the wound dressing system of Embodiment WW, wherein the first and second lateral edges extend substantially parallel to the longitudinal axis.

Embodiment YY is the wound dressing system of Embodiment WW or Embodiment XX, wherein the plurality of uncovered portions including at least two uncovered portions along the first lateral edge and at least two uncovered portions along the second lateral edge.

Embodiment ZZ is the wound dressing of any one of Embodiments WW through YY, wherein at least one outer spoke of the dressing support layer extends along a portion of the first lateral edge or the second lateral edge.

Embodiment AAA is the wound dressing system of any one of Embodiments WW through ZZ, wherein at least one inner spoke extends toward the first lateral edge substantially opposite an inner spoke extending toward the second lateral edge.

Embodiment BBB is the wound dressing system of Embodiment AAA, wherein the at least one of the inner spoke extending toward the first lateral edge and the inner spoke opposite thereof extending toward the second lateral edge each comprises a visible indicium.

Embodiment CCC is the wound dressing system of any one of Embodiments WW through BBB, wherein at least three inner spokes extend from a first medial portion toward the first lateral edge and at least three inner spokes extend from a second medial portion toward the second lateral edge.

Objects and advantages of this invention are further illustrated by the following examples, but the particular materials and amounts thereof recited in these examples, as well as other conditions and details, should not be construed to unduly limit this invention.

EXAMPLES

Example 1

A wound dressing system similar to the wound dressing system 5000 shown in FIG. 14 was made using materials and processes similar to those described in Example 1 of U.S. Pat. No. 5,531,855, with the exception that the die used to cut the dressing support layer and the final product was modified to produce the pattern of covered and uncovered regions of the backing as shown in FIG. 14 of the present disclosure. Prior to heat-sealing the dressing support layer to the backing, a bond-block comprising 3M MICROPORE Tape (3M Company, St. Paul, Minn.) was laminated along a region (i.e., the bond-block zone 45 shown in FIG. 1 of the present disclosure) proximate the central axis of the dressing.

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

The invention claimed is:

1. A wound dressing system, comprising:
a rectangular wound dressing having a first end, a second end opposite the first end, and a longitudinal axis extending from the first end to the second end; the wound dressing comprising:
an elastic film backing, the backing comprising a first major surface, a second major surface opposite the first major surface, and a perimeter that includes first and second lateral edges, the first and second lateral edges extending from the first end to the second end;
an adhesive disposed on the first major surface; and
a dressing support layer comprising juxtaposed first and second sections removably mounted on the second major surface of the backing, wherein the juxtaposed first and second sections define a gap between the first and second sections, wherein the gap extends substantially from the first end to the second end;
wherein each of the first and second sections comprises a medial portion extending from at or adjacent to the first end to at or adjacent to the second end, and at least four spokes extending perpendicular therefrom toward the first and second lateral edges, wherein the at least four spokes comprise a first outer spoke extending substantially to and along the perimeter at the first end, a second outer spoke extending substantially to and along the perimeter at the second end, and at least two spaced-apart inner spokes disposed therebetween;
wherein at least two of the at least four spokes of each of the first and second sections extend beyond the lateral edge to form peripheral support layer tabs;
wherein the dressing support layer defines a plurality of covered portions and uncovered portions of the backing.

2. The wound dressing system of claim 1, wherein at least one of the inner spokes of the first section extends toward the first lateral edge substantially opposite one of the inner spokes of the second section.

3. The wound dressing system of claim 2, wherein at least one of the inner spokes of the first section and a corresponding inner spoke opposite thereof in the second section each comprises a visible indicium.

4. The wound dressing system of claim 3:
wherein the dressing support layer comprises a first inner spoke of the first section and a second inner spoke of the second section;
wherein both the first inner spoke and second inner spoke comprise lines of indicia;
wherein the first inner spoke extends away from the longitudinal axis opposite the second inner spoke;
wherein cutting the system along a line defined by the lines of indicia creates two smaller wound dressing systems of approximately equal size.

5. The wound dressing system of claim 1, wherein the first outer spoke of at least one of the first and second sections extends along a portion of the perimeter of the backing at the first end.

6. The wound dressing system of claim 5, wherein the second outer spoke of at least one of the first and second sections extends along a portion of the perimeter of the backing at the second end.

7. The wound dressing system of claim 1, wherein the first outer spoke extends along at least 20 percent of the perimeter of the backing at the first end.

8. The wound dressing system of claim 7, wherein the second outer spoke extends along at least 20 percent of the perimeter at the second end.

9. The wound dressing of claim 1, wherein the first and second lateral edges extend substantially parallel to the longitudinal axis.

10. The wound dressing system of claim 1, wherein the plurality of uncovered portions including at least two uncovered portions along the first lateral edge and at least two uncovered portions along the second lateral edge.

11. The wound dressing of claim 1, wherein at least one outer spoke of at least one section of the dressing support layer extends along a portion of the first lateral edge or the second lateral edge.

12. The wound dressing system of claim 1, wherein the first outer spoke of the first section, at the first end of the dressing, comprises a peripheral support layer tab; wherein one of the at least two spaced-apart inner spokes has a peripheral support layer tab.

13. The wound dressing system of claim 1, wherein each of the first and second sections of the dressing support layer comprises three inner spokes.

14. The wound dressing system of claim 1, wherein at least one of the inner spokes of each of the first and second sections extends substantially along a line that is perpendicular to the longitudinal axis.

15. The wound dressing system of claim 1, wherein a plurality of inner spokes of each of the first and second sections extend along lines that are each substantially perpendicular to the longitudinal axis.

16. The wound dressing system of claim 1, wherein the plurality of uncovered portions includes an uncovered portion along the perimeter at the first end or at the second end.

17. The wound dressing of claim 1, wherein the plurality of uncovered portions includes an uncovered portion that forms a part of the gap.

18. The wound dressing system of claim 1, wherein the dressing support layer comprises a bridge member overlapping the backing and spaced apart from the medial portion, the bridge member connecting a first spoke to a second spoke adjacent the first spoke; wherein the first spoke, the second spoke, the medial portion, and the bridge member define an uncovered portion of the backing.

19. The wound dressing system of claim 1, further comprising a bond-block zone on the second major surface of the backing, wherein the support layer is not bonded to the second major surface of the backing in the bond-block zone.

20. The wound dressing system of claim 1, wherein the gap forms a line of symmetry for the dressing support layer.

* * * * *

UNITED STATES PATENT AND TRADEMARK OFFICE
CERTIFICATE OF CORRECTION

PATENT NO. : 10,561,536 B2
APPLICATION NO. : 15/107490
DATED : February 18, 2020
INVENTOR(S) : David Holm It is certified that error appears in the above-identified patent and that said Letters Patent is hereby corrected as shown below:

On the Title Page

Related U.S. Application Data
(60)                    Delete "61/992,360," and insert -- 61/922,360, --, therefor.

In the Specification

Column 1
Line 59                 After "sites" insert -- . --.

Column 3
Line 57                 After "structure" insert -- . --.

Column 13
Line 57                 Delete "less)" and insert -- less). --, therefor.

Column 22
Line 26                 Delete "f" and insert -- of --, therefor.

Column 24
Line 65                 Delete "Germany)" and insert -- Germany). --, therefor.

Column 26
Line 16 (Approx.)       Delete "The" and insert -- the --, therefor.

Column 28
Line 4                  Delete "edge.)" and insert -- edge. --, therefor.

Signed and Sealed this
Twentieth Day of July, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,561,536 B2

In the Claims

<u>Column 32</u>
Claim 9, Line 26        After "dressing" insert -- system --.
Claim 11, Line 33       After "dressing" insert -- system --.
Claim 17, Line 56       After "dressing" insert -- system --.